(12) United States Patent
Erramilli et al.

(10) Patent No.: US 9,949,731 B2
(45) Date of Patent: Apr. 24, 2018

(54) SYSTEMS AND METHODS FOR MANIPULATING BONE

(71) Applicant: Medos International Sarl, Le Locle (CH)

(72) Inventors: Seetal Erramilli, Melbourne (AU); Grant Mellor, Eltham (AU); Frank Spratt, Middleboro, MA (US)

(73) Assignee: Medos International Sàrl, Le Locle (CH)

( * ) Notice: Subject to any disclaimer, the term of this patent is extended or adjusted under 35 U.S.C. 154(b) by 166 days.

(21) Appl. No.: 14/876,914

(22) Filed: Oct. 7, 2015

(65) Prior Publication Data
US 2017/0100116 A1    Apr. 13, 2017

(51) Int. Cl.
*A61B 17/02*    (2006.01)
*A61B 17/70*    (2006.01)
(Continued)

(52) U.S. Cl.
CPC .......... *A61B 17/025* (2013.01); *A61B 17/708* (2013.01); *A61B 17/7032* (2013.01);
(Continued)

(58) Field of Classification Search
CPC .............. A61B 17/708; A61B 17/7082; A61B 17/7077; A61B 17/7076; A61B 17/025;
(Continued)

(56) References Cited

U.S. PATENT DOCUMENTS

| 6,736,820 B2 | 5/2004 | Biedermann et al. |
| 6,974,460 B2 | 12/2005 | Carbone et al. |

(Continued)

FOREIGN PATENT DOCUMENTS

| EP | 1935358 A1 | 6/2008 |
| EP | 2 286 748 A1 | 2/2011 |
| WO | 2014/052117 A1 | 4/2014 |

OTHER PUBLICATIONS

International Search Report for Application No. PCT/US2016/055412, dated May 10, 2017 (8 pages).
(Continued)

*Primary Examiner* — Ellen C Hammond
(74) *Attorney, Agent, or Firm* — Nutter McClennen & Fish LLP

(57) ABSTRACT

Systems and methods are disclosed in which a distraction sleeve can be attached to a bone anchor assembly to lock or limit the polyaxial degree of freedom of the bone anchor assembly and facilitate true parallel distraction. In some embodiments, the distraction sleeve can lock polyaxial movement of the bone anchor assembly without directly engaging the shank of the bone anchor assembly, without directly engaging the exterior of the receiver member of the bone anchor assembly, and/or without requiring that a rod or closure mechanism be installed in the bone anchor assembly. The distraction sleeve can be preloaded onto the bone anchor assembly prior to inserting the bone anchor assembly using a selectively detachable driver, thereby providing simplified, streamlined insertion and facilitating use with protection and/or retraction sheaths. Countertorque tubes, torque wrenches, and other related instrumentation are also disclosed herein.

24 Claims, 14 Drawing Sheets

(51) Int. Cl.
 *A61B 90/00* (2016.01)
 *A61B 17/56* (2006.01)
 *A61B 17/68* (2006.01)

(52) U.S. Cl.
 CPC ...... *A61B 17/7035* (2013.01); *A61B 17/7074* (2013.01); *A61B 17/7082* (2013.01); *A61B 2017/0256* (2013.01); *A61B 2017/564* (2013.01); *A61B 2017/681* (2013.01); *A61B 2090/037* (2016.02)

(58) Field of Classification Search
 CPC ............ A61B 17/7032; A61B 17/7034; A61B 17/7037; A61B 2017/0256
 See application file for complete search history.

(56) References Cited

U.S. PATENT DOCUMENTS

| | | | |
|---|---|---|---|
| 7,179,261 B2 | 2/2007 | Sicvol et al. | |
| 2005/0131408 A1* | 6/2005 | Sicvol | A61B 17/7032 606/86 A |
| 2006/0079909 A1 | 4/2006 | Runco et al. | |
| 2010/0114174 A1 | 5/2010 | Jones et al. | |
| 2011/0046683 A1* | 2/2011 | Biedermann | A61B 17/7035 606/305 |
| 2011/0288599 A1 | 11/2011 | Michielli et al. | |
| 2013/0053901 A1 | 2/2013 | Cormier et al. | |
| 2013/0096618 A1 | 4/2013 | Chandanson et al. | |
| 2013/0172935 A1* | 7/2013 | Matthis | A61B 17/7032 606/278 |
| 2014/0094849 A1* | 4/2014 | Spratt | A61B 17/7035 606/257 |
| 2014/0277137 A1 | 9/2014 | Stad et al. | |

OTHER PUBLICATIONS

[No Author Listed] Matrix Spine System—Degenerative. A posterior pedicle screw and rod fixation system. Surgical Technique Guide. Synthes Spine, 60 pages, 2010.

Written Opinion for International Application No. PCT/US2016/055412, dated May 10, 2017 (11 pages).

* cited by examiner

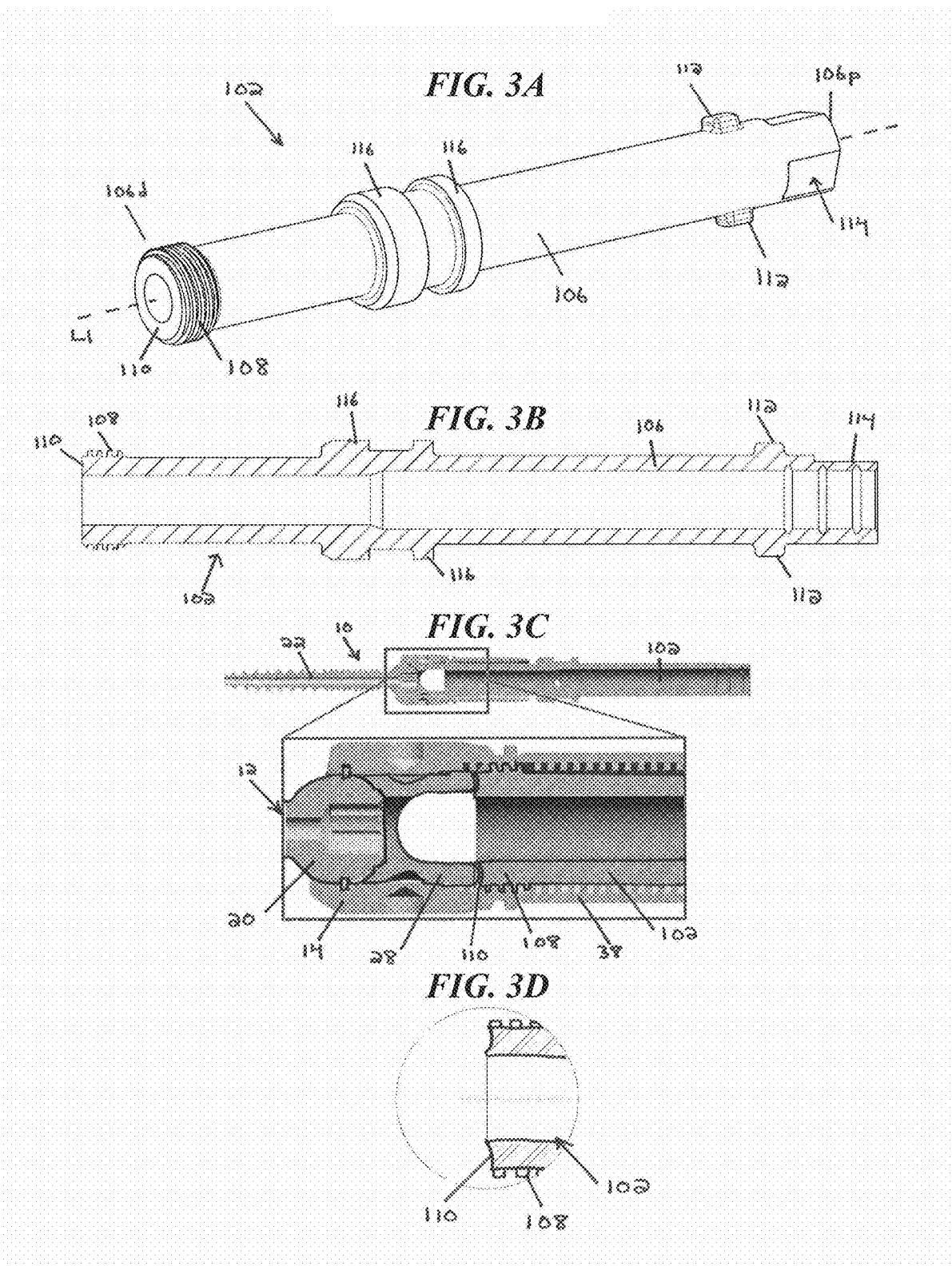

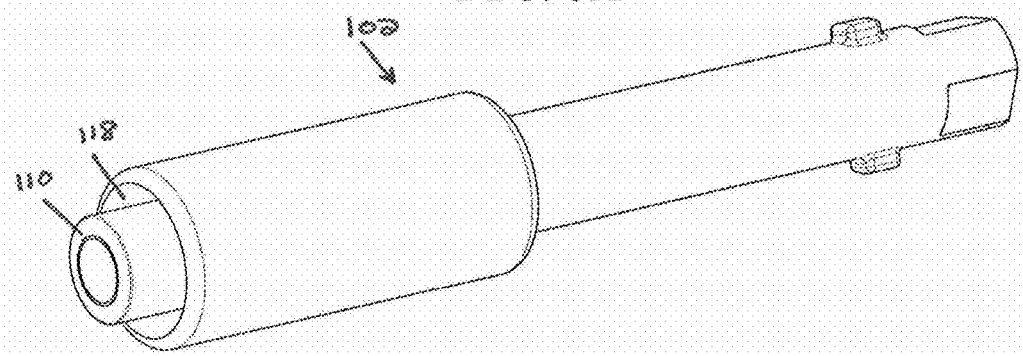
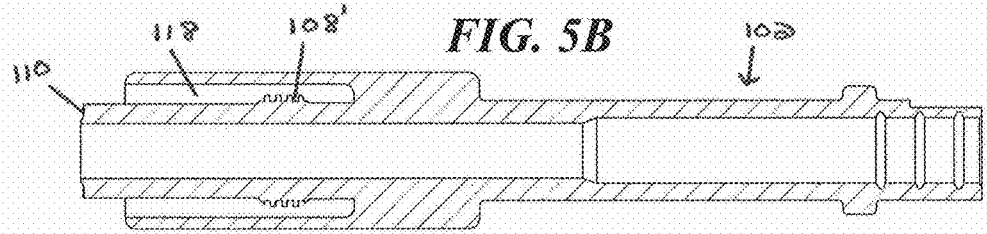
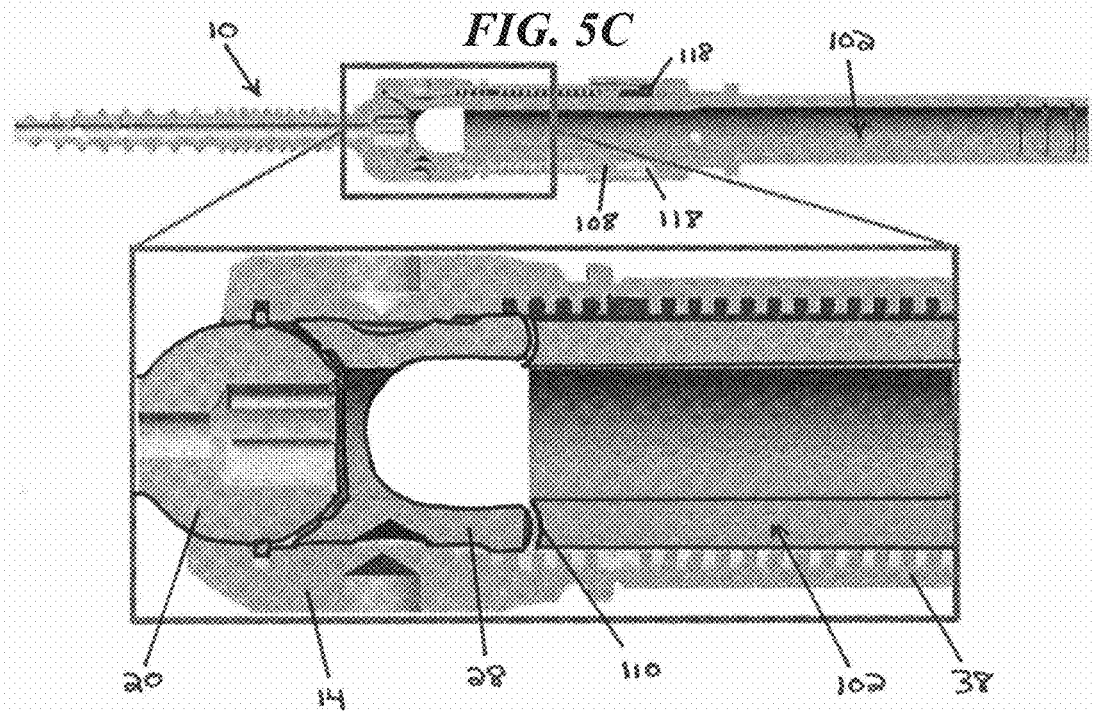

SYSTEMS AND METHODS FOR MANIPULATING BONE

FIELD

Systems and methods for manipulating bone are disclosed herein. For example, systems and methods for distracting vertebrae during spinal surgery are disclosed.

BACKGROUND

Bone anchor assemblies can be used in orthopedic surgery to fix bone during healing, fusion, or other processes. In spinal surgery, for example, bone anchor assemblies can be used to secure a spinal fixation element to one or more vertebrae to rigidly or dynamically stabilize the spine.

Bone anchor assemblies can also be used as an engagement point for manipulating bone (e.g., distracting, compressing, or rotating one vertebra with respect to another vertebra, reducing fractures in a long bone, and so forth). In these instances, a distractor or other instrument can be used to apply a manipulation force to the bone anchor assembly and, by extension, to the bone in which the bone anchor assembly is implanted.

Traditional bone anchor distraction systems typically rely on gripping the outer portion of a polyaxial receiver member of the bone anchor assembly. This can be undesirable in some instances, as there is a potential for interference to occur in situations where adjacent receiver members abut against one another (especially at L5-S1) resulting in an inability to properly place the distraction instrument over the receiver member. In addition, distraction systems that rely on gripping the outer portion of the receiver member cannot achieve true parallel distraction unless rods and set screws are also placed within the receiver member to lock off its polyaxial degree of freedom. The requirement that rods and set screws be in place in order to achieve true parallel distraction can be cumbersome for surgeons who prefer to distract off of the bone anchor assemblies to maximize visualization in preparation for any discectomy and interbody work (e.g., PLIF or TLIF procedures). Other distraction systems attempt to achieve true parallel distraction in the absence of rods and set screws by directly engaging with the shank of the bone anchor assembly. This can also be undesirable, however, as the extensions of the distraction instrument can mechanically interfere with one another, especially in regions of the lumbar spine with high lordosis (e.g., L5-S1), making distraction very difficult to perform.

Another shortcoming of existing distraction systems is that they generally can only be attached to a bone anchor assembly after it has been inserted into the bone. Feeding a distraction tool over a receiver member of a bone anchor assembly after it has already been inserted into the bone can be difficult and time-consuming for the surgeon.

There is a continual need for improved systems and related methods for manipulating bone.

SUMMARY

Systems and methods are disclosed in which a distraction sleeve can be attached to a bone anchor assembly to lock or limit the polyaxial degree of freedom of the bone anchor assembly and facilitate true parallel distraction. In some embodiments, the distraction sleeve can lock polyaxial movement of the bone anchor assembly without directly engaging the shank of the bone anchor assembly, without directly engaging the exterior of the receiver member of the bone anchor assembly, and/or without requiring that a rod or closure mechanism be installed in the bone anchor assembly. The distraction sleeve can be preloaded onto the bone anchor assembly prior to inserting the bone anchor assembly using a selectively detachable driver, thereby providing simplified, streamlined insertion and facilitating use with protection and/or retraction sheaths. Countertorque tubes, torque wrenches, and other related instrumentation are also disclosed herein.

In some embodiments, a bone manipulation system includes a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element; and a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument.

A distal-facing surface of the distraction sleeve can engage proximal-facing surfaces of the first and second arms of the compression cap when the sleeve is seated in the receiver member.

The distal-facing surface of the distraction sleeve can have a concave longitudinal cross-section that corresponds with a convex longitudinal cross-section of the first and second arms of the compression cap.

The distraction sleeve can have a length sufficient to extend to a skin surface of a patient when the distal end of the distraction sleeve is seated in the receiver member and the bone anchor is implanted in a bone of the patient.

The distraction sleeve can include an external thread that threads into an internal thread of the receiver member.

The external thread can be formed at the distal end of the distraction sleeve.

The distraction sleeve can include an external thread that threads into an internal thread of first and second opposed extension tabs that extend proximally from the receiver member.

The extension tabs can have free proximal ends and define a slot therebetween through which a rod can be reduced into the receiver member.

The external thread can be spaced a distance apart from the distal end of the distraction sleeve such that the external thread engages proximal ends of the extension tabs when the distal end of the distraction sleeve is seated in the receiver member.

The distraction sleeve can include a tubular pocket sized and positioned to receive at least a portion of each extension tab when the distal end of the distraction sleeve is seated in the receiver member.

The external thread can be formed within the tubular pocket.

The system can include a driver instrument that includes a driver shaft insertable through the distraction sleeve and the receiver member and having a distal drive tip configured to engage the bone anchor for driving the bone anchor into bone; and a body portion in which the driver shaft is rotatably disposed, the body portion having a mating feature configured to engage a corresponding mating feature of the distraction sleeve to selectively couple the body portion to the distraction sleeve.

The mating feature of the body portion can include at least one slot and the mating feature of the distraction sleeve can include at least one projection that extends radially outward from the distraction sleeve.

The at least one slot can include a first longitudinal portion open to a distal end of the body portion, a second longitudinal portion that is closed to the distal end of the body portion, and a lateral portion connecting the first and second longitudinal portions.

The body portion can house a spring configured to bias the body portion proximally with respect to the driver shaft.

The system can include a torque wrench having a drive tip configured to engage a driving interface of the distraction sleeve and an alignment pin that extends distally from the drive tip to engage a driving interface formed in the bone anchor when the torque wrench is coupled to the distraction sleeve and the distraction sleeve is coupled to the bone anchor assembly.

The system can include a retraction sheath having a tubular frame rotatably disposed over an external surface of the distraction sleeve and having at least one wing extending laterally from the tubular frame to retract tissue.

The at least one wing can include first and second wings that define a working channel therebetween.

The tubular frame can include a relief sized to accommodate the receiver member of the bone anchor assembly such that the at least one wing of the retraction sheath extends at least to a distal end of the receiver member when the retraction sheath is installed over the receiver member.

In some embodiments, a method of adjusting a position or orientation of bone can include rotating a distraction sleeve to advance the distraction sleeve into a receiver member of a bone anchor assembly such that a distal-facing end surface of the distraction sleeve bears against opposed arms of a compression cap disposed in the receiver member, thereby locking polyaxial movement of the bone anchor assembly; driving the bone anchor assembly into a bone; and after driving the bone anchor assembly into the bone, applying a force to the distraction sleeve to adjust a position or orientation of the bone.

The distraction sleeve can be coupled to the bone anchor assembly to lock said polyaxial movement before driving the bone anchor assembly into the bone.

The distraction sleeve can be coupled to the bone anchor assembly to lock said polyaxial movement after driving the bone anchor assembly into the bone.

The force can be applied without directly engaging a shank of the bone anchor assembly, without directly engaging an exterior of the receiver member of the bone anchor assembly, and without installing a rod or closure mechanism in the receiver member of the bone anchor assembly.

Advancing the distraction sleeve can include threading an external thread of the distraction sleeve into at least one of (i) an internal thread of the receiver member and (ii) an internal thread of first and second opposed extension tabs that extend proximally from the receiver member.

The method can include at least partially positioning first and second opposed extension tabs that extend proximally from the receiver member within a tubular pocket defined by the distraction sleeve.

Driving the bone anchor can include inserting a driver shaft of a driver instrument through the distraction sleeve to engage a drive tip of the driver shaft with a driving interface of the bone anchor assembly and coupling a body portion of the driver instrument to the distraction sleeve.

Coupling the body portion to the distraction sleeve can include advancing the body portion distally with respect to the distraction sleeve against the bias of a spring to slide a projection of the distraction sleeve within a slot formed in the body portion, rotating the body portion relative to the distraction sleeve, and releasing the body portion to allow the spring to urge the body portion proximally with respect to the distraction sleeve.

The method can include sliding a torque tube over the distraction sleeve and coupling the torque tube to the receiver member such that the torque tube cannot rotate relative to the receiver member and coupling a torque wrench to a driving interface of the distraction sleeve to rotate the distraction sleeve and advance the distraction sleeve into the receiver member.

The torque wrench can include an alignment pin that extends longitudinally through the distraction sleeve to engage a driving interface of a shank portion of the bone anchor assembly.

The method can include retracting tissue proximate to the bone using one or more wings that extend from a retraction sheath disposed over the distraction sleeve.

The present invention further provides systems and methods as claimed.

BRIEF DESCRIPTION OF THE DRAWINGS

The invention will be more fully understood from the following detailed description taken in conjunction with the accompanying drawings, in which:

FIG. 3A is a perspective view of a distraction sleeve;

FIG. 3B is a sectional view of the distraction sleeve of FIG. 3A;

FIG. 3C is a sectional view with magnified inset of the distraction sleeve of FIG. 3A coupled to the bone anchor assembly of FIG. 1A;

FIG. 3D is a magnified sectional view of the distal end of the distraction sleeve of FIG. 3A;

FIG. 5A is a perspective view of a distraction sleeve;

FIG. 5B is a sectional view of the distraction sleeve of FIG. 5A;

FIG. 5C is a sectional view with magnified inset of the distraction sleeve of FIG. 5A coupled to the bone anchor assembly of FIG. 1A;

FIGS. 14A-14K schematically illustrate a method of performing surgery in which:

FIG. 14A is a perspective view of preparing a bone;

FIG. 14B is a perspective view of a distraction sleeve coupled to a bone anchor assembly;

FIG. 14C is a perspective view of a driver instrument being coupled to the distraction sleeve;

FIG. 14D is a perspective view of a protection sheath installed over the distraction sleeve;

FIG. 14E is a perspective view of the bone anchor assembly installed in the bone and the driver instrument being separated from the distraction sleeve;

FIG. 14F is a perspective view of the bone anchor assembly and distraction sleeve left behind once the driver instrument is removed;

FIG. 14G is a perspective view of a second bone anchor assembly and distraction sleeve installed in an adjacent vertebra;

FIG. 14H is a perspective view of a distraction instrument;

FIG. 14I is a perspective view of the distraction instrument inserted into the first and second distraction sleeves;

FIG. 14J is a perspective view of the distraction instrument being removed from the first and second distraction sleeves; and FIG. 14K is a perspective view of a countertorque tube and torque wrench being used to remove the first distraction sleeve from the first bone anchor assembly.

DETAILED DESCRIPTION

Systems and methods are disclosed in which a distraction sleeve can be attached to a bone anchor assembly to lock or limit the polyaxial degree of freedom of the bone anchor assembly and facilitate true parallel distraction. In some embodiments, the distraction sleeve can lock polyaxial movement of the bone anchor assembly without directly engaging the shank of the bone anchor assembly, without directly engaging the exterior of the receiver member of the bone anchor assembly, and/or without requiring that a rod or closure mechanism be installed in the bone anchor assembly. The distraction sleeve can be preloaded onto the bone anchor assembly prior to inserting the bone anchor assembly using a selectively detachable driver, thereby providing simplified, streamlined insertion and facilitating use with protection and/or retraction sheaths. Countertorque tubes, torque wrenches, and other related instrumentation are also disclosed herein.

Certain exemplary embodiments will now be described to provide an overall understanding of the principles of the structure, function, manufacture, and use of the systems and methods disclosed herein. One or more examples of these embodiments are illustrated in the accompanying drawings. Those of skill in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Prior Art Bone Anchor Assembly

Figure 1A:
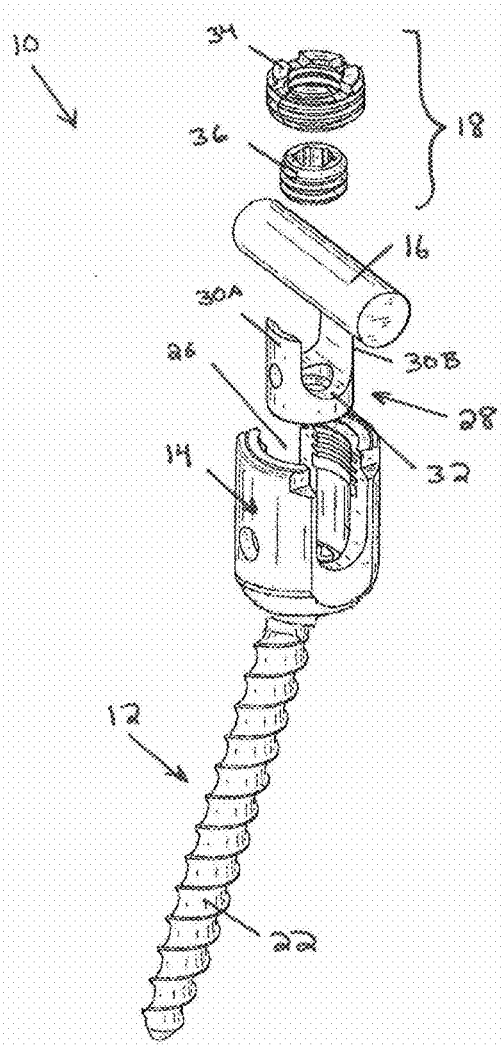
FIG. 1A is an exploded perspective view of a prior art bone anchor assembly.
Figure 1B:
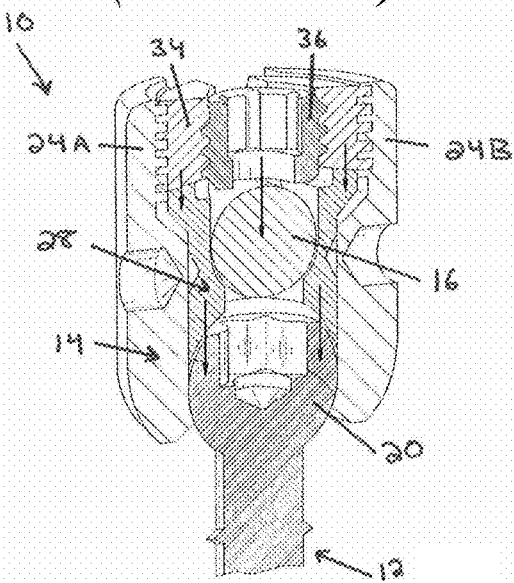
FIG. 1B is a sectional view of the bone anchor assembly of FIG. 1A.
Figure 1C:
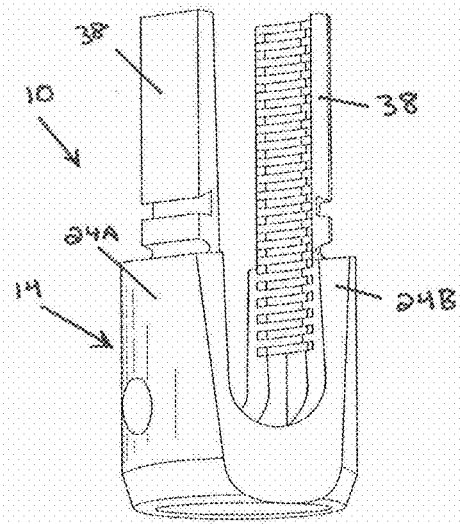
FIG. 1C is a perspective view of the bone anchor assembly of FIG. 1A shown with extension tabs.

FIGS. 1A-1C illustrate a prior art bone anchor assembly 10 with which the systems and methods disclosed herein can be used. It will be appreciated that the illustrated bone anchor assembly 10 is exemplary and that the systems and methods herein can be used with any of a variety of types of bone anchor assemblies.

The illustrated bone anchor assembly 10 includes a bone anchor 12, a receiver member 14 for receiving a spinal fixation element, such as a spinal rod 16, to be coupled to the bone anchor 12, and a closure mechanism 18 to capture a spinal fixation element within the receiver member 14 and fix the spinal fixation element with respect to the receiver member 14. The bone anchor 12 includes a proximal head 20 and a distal shaft 22 configured to engage bone. The receiver member 14 has a proximal end having a pair of spaced apart arms 24A, 24B defining a recess 26 therebetween and a distal end having a distal end surface defining an opening through which at least a portion of the bone anchor 12 extends. The closure mechanism 18 can be positionable between and can engage the arms 24A, 24B to capture a spinal fixation element, e.g., a spinal rod 16, within the receiver member 14 and fix the spinal fixation element with respect to the receiver member 14.

The proximal head 20 of the bone anchor 12 is generally in the shape of a truncated sphere having a planar proximal surface and an approximately spherically-shaped distal surface. The illustrated bone anchor assembly 10 is a polyaxial bone screw designed for posterior implantation in the pedicle or lateral mass of a vertebra. The proximal head 20 of the bone anchor 12 engages the distal end of the receiver member 14 in a ball and socket like arrangement in which the proximal head and the distal shaft 22 can pivot relative to the receiver member 14. The distal surface of the proximal head 20 of the bone anchor 12 and a mating surface within the distal end of the receiver member 14 can have any shape that facilitates this arrangement, including, for example, spherical (as illustrated), toroidal, conical, frustoconical, and any combinations of these shapes.

The distal shaft 22 of the bone anchor 12 can be configured to engage bone and, in the illustrated embodiment, includes an external bone engaging thread. The thread form for the distal shaft 22, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 22 can also include other structures for engaging bone, including a hook. The distal shaft 22 of the bone anchor 12 can be cannulated, having a central passage or cannula extending the length of the bone anchor to facilitate delivery of the bone anchor over a guidewire in, for example, minimally-invasive procedures. Other components of the bone anchor assembly 10, including, for example, the closure mechanism 18, the receiver member 14, and the compression member or cap 28 (discussed below) can be cannulated or otherwise have an opening to permit delivery over a guidewire. The distal shaft 22 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 22. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated by reference herein. The distal shaft 22 of the bone anchor 12 can also be coated with materials to permit bone growth, such as, for example, hydroxyapatite, and the bone anchor assembly 10 can be coated partially or entirely with anti-infective materials, such as, for example, tryclosan.

The proximal end of the receiver member 14 includes a pair of spaced apart arms 24A, 24B defining a U-shaped recess 26 therebetween for receiving a spinal fixation element, e.g., a spinal rod 16. Each of the arms 24A, 24B can extend from the distal end of the receiver member 14 to a free end. The outer surfaces of each of the arms 24A, 24B can include a feature, such as a recess, dimple, notch, projection, or the like, to facilitate connection of the receiver member 14 to instruments. For example, the outer surface of each arm 24A, 24B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 14 includes a distal end surface which is generally annular in shape defining a circular opening through which at least a portion of the bone anchor 12 extends. For example, the distal shaft 22 of the bone anchor 12 can extend through the opening.

The bone anchor 12 can be selectively fixed relative to the receiver member 14. Prior to fixation, the bone anchor 12 is movable relative to the receiver member 14 within a cone of angulation generally defined by the geometry of the distal end of the receiver member and the proximal head 20 of the bone anchor 12. The bone anchor assembly 10 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly 10 can be a conventional (non-biased) polyaxial screw in which the bone anchor 12 pivots in the same amount in every direction.

The spinal fixation element, e.g., the spinal rod 16, can either directly contact the proximal head 20 of the bone anchor 12 or can contact an intermediate element, e.g., a compression member 28. The compression member 28 can be positioned within the receiver member 14 and interposed between the spinal rod 16 and the proximal head 20 of the bone anchor 12 to compress the distal outer surface of the proximal head 20 into direct, fixed engagement with the distal inner surface of the receiver member 14. The compression member 28 can include a pair of spaced apart arms 30A and 30B defining a U-shaped seat 32 for receiving the spinal rod 16 and a distal surface for engaging the proximal head 20 of the bone anchor 12.

The proximal end of the receiver member 14 can be configured to receive a closure mechanism 18 positionable between and engaging the arms 24A, 24B of the receiver member 14. The closure mechanism 18 can be configured to capture a spinal fixation element, e.g., a spinal rod 16, within the receiver member 14, to fix the spinal rod relative to the receiver member 14, and to fix the bone anchor 12 relative to the receiver member 14. The closure mechanism 18 can be a single set screw having an outer thread for engaging an inner thread provided on the arms 24A, 24B of the receiver member 14. In the illustrated embodiment, however, the closure mechanism 18 includes an outer set screw 34 operable to act on the compression member 28 and an inner set screw 36 operable to act on the rod 16. The receiver member 14 can include, can be formed integrally with, or can be coupled to one or more extension tabs 38 (shown in FIG. 1C) that extend proximally from the receiver member 14 to functionally extend the length of the arms 24A, 24B. The extension tabs 38 can facilitate installation and assembly of a fixation or stabilization construct and can be removed prior to completing a surgical procedure.

The bone anchor assembly 10 can be used with a spinal fixation element such as rigid spinal rod 16. Alternatively, the spinal fixation element can be a dynamic stabilization member that allows controlled mobility between the instrumented vertebrae.

In use, the bone anchor assembly 10 can be assembled such that the distal shaft 22 extends through the opening in the distal end of the receiver member 14 and the proximal head 20 of the bone anchor 12 is received in the distal end of the receiver member 14. A driver instrument can be fitted with the bone anchor 12 to drive the bone anchor into bone. The compression member 28 can be positioned within the receiver member 14 such that the arms 30A, 30B of the compression member are aligned with the arms 24A, 24B of the receiver member 14 and the lower surface of the compression member 28 is in contact with the proximal head 20 of the bone anchor 12. A spinal fixation element, e.g., the spinal rod 16, can be located in the recess 26 of the receiver member 14. The closure mechanism 18 can be engaged with the inner thread provided on the arms 24A, 24B of the receiver member 14. A torsional force can be applied to the outer set screw 34 to move it within the recess 26 so as to force the compression member 28 onto the proximal head 20 of the bone anchor 12, thereby locking the angular position of the bone anchor 12 relative to the receiver member 14. A torsional force can be applied to the inner set screw 36 to force the spinal rod 16 into engagement with the compression member 28 and thereby fix the spinal rod 16 relative to the receiver member 14.

The instruments disclosed herein can be configured to operate in conjunction with bone anchor assemblies of the type described above or other types known in the art. Exemplary bone anchor assemblies include monoaxial screws, polyaxial screws, uniplanar screws, favored-angle screws, and/or any of a variety of other bone anchor types known in the art. Further information on favored-angle screws can be found in U.S. Patent Application Publication No. 2013/0096618, filed on Oct. 9, 2012, which is hereby incorporated by reference herein. Bone anchor assemblies are sometimes referred to herein simply as "bone anchors."

Systems and Methods for Manipulating Bone

Figure 2:
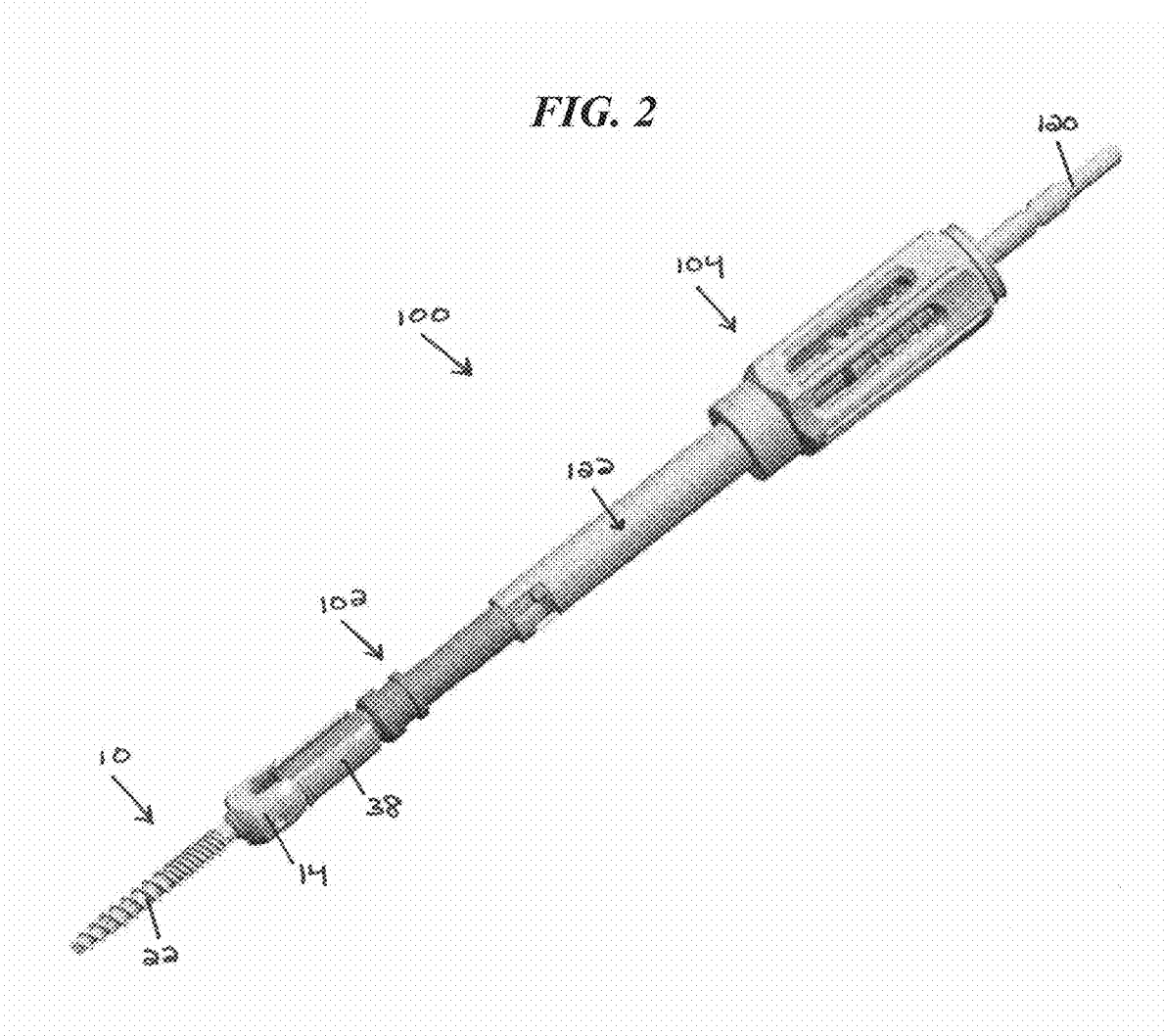
FIG. 2 is a perspective view of a distraction system coupled to the bone anchor assembly of FIG. 1A.

FIG. 2 illustrates an exemplary embodiment of a distraction system 100, which is shown with a bone anchor assembly 10 of the type described above. While generally referred to as a "distraction" system, it will be appreciated that the system 100 can be used for any of a variety of bone manipulation tasks, such as distracting, compressing, rotating, reducing, etc.

The system 100 generally includes a distraction sleeve 102 and a driver instrument 104 for driving the bone anchor assembly 10. In some embodiments, the system 100 can advantageously allow the bone anchor assembly 10 to be driven into bone with the distraction sleeve 102 pre-attached to the bone anchor assembly. The driver instrument 104 can then be separated from the rest of the system, leaving the distraction sleeve 102 in place to receive a distractor or other instrument.

Distraction Sleeve

The distraction sleeve 102 is shown in more detail in FIGS. 3A-3D. In use, the distraction sleeve 102 can be coupled to a bone anchor assembly, before or after implanting the bone anchor assembly in bone, to provide an engagement point for manipulating bone to which the bone anchor assembly is coupled. The distraction sleeve 102 can be generally in the form of an elongate tubular body 106 having a proximal end 106p and a distal end 106d and extending along a longitudinal axis L1. The distraction sleeve can have a length that is sufficient to extend from a skin incision of a patient to proximate a bone surface of the patient.

The distraction sleeve 102 can include a mating feature for selectively attaching or coupling the distraction sleeve to a bone anchor assembly. In the illustrated embodiment, the distraction sleeve 102 includes a threaded distal end 108 configured to threadably engage internal threads of the receiver member 14 of the bone anchor assembly 10, or the internal threads of extension tabs 38 extending from the receiver member. When coupled to the receiver member 14, the distal-facing terminal end surface 110 of the distraction sleeve 102 abuts with the proximal-facing terminal end surface of the compression member 28, as shown in FIG. 3C. Accordingly, as the distraction sleeve 102 is threaded into the receiver member 14, it urges the compression member 28 distally against the head 20 of the bone anchor 12, thereby locking out the polyaxial degree of freedom of the bone anchor assembly 10, or at least generating resistance to polyaxial movement of the bone anchor assembly. In other words, the distal portion of the distraction sleeve 102 performs a similar function to the outer set screw 34 shown in FIGS. 1A-1B.

The distraction sleeve 102 can thus lock the polyaxial degree of freedom of the bone anchor assembly 10 without directly engaging the shank 22 or head 20 of the bone anchor 12, without directly engaging the exterior of the receiver member 14, and without the need to install a spinal rod or closure mechanism in the receiver member 14. It will be appreciated that the distraction sleeve 102 can also be used without engaging the compression member 28 at all or without locking or limiting the polyaxial degree of freedom of the bone anchor assembly 10 by not fully advancing the distraction sleeve into the receiver member 14.

As shown in FIG. 3D, the distal-facing terminal end surface 110 of the distraction sleeve 102 can have a shape that mirrors or otherwise corresponds to the shape of the proximal-facing terminal end surface of the compression member 28. For example, the end of the distraction sleeve 102 can have a concave longitudinal cross section such that it defines a recess in which the corresponding convex portion of the compression member 28 can be received.

The distraction sleeve 102 can include a mating feature for selectively attaching or coupling the distraction sleeve to the driver instrument 104. For example, the distraction sleeve 102 can include one or more ears 112 that project radially outward from the exterior surface of the distraction sleeve. The ears 112 can be configured to engage with corresponding recesses or slots formed in the driver instrument 104, as detailed below. The distraction sleeve 102 can be coupled to the driver instrument 104 in various other ways, such as via a threaded or snap-fit connection.

A driving interface 114 can be included in the distraction sleeve 102 to allow torque to be applied to the distraction sleeve, e.g., for the purpose of threading or unthreading the distraction sleeve to or from the receiver member 14. The driving interface 114 can be defined by one or more flats formed in the sidewall of the sleeve 102. The illustrated sleeve 102 includes three flats spaced equally about the circumference of the sleeve to define a tri-lobe structure for applying torque to the sleeve. In other embodiments, the sleeve 102 can include one, two, or four or more flats, or can include other types of male or female driving interfaces.

The distraction sleeve 102 can also include one or more protrusions 116 or other features for selectively coupling the distraction sleeve to a protection sheath or a retraction sheath, as detailed further below.

Figure 4A:
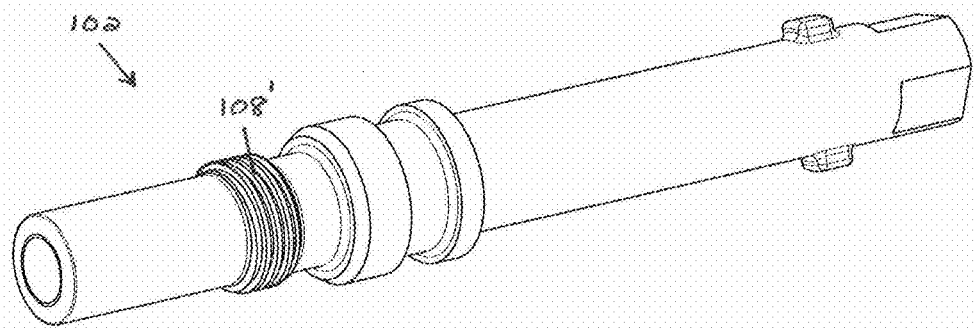
FIG. 4A is a perspective view of a distraction sleeve.
Figure 4B:
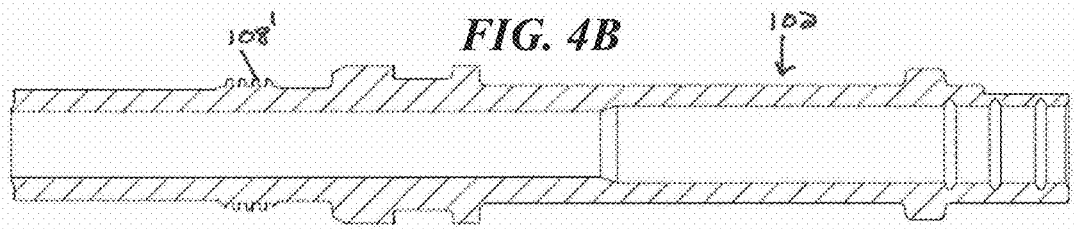
FIG. 4B is a sectional view of the distraction sleeve of FIG. 4A.
Figure 4C:
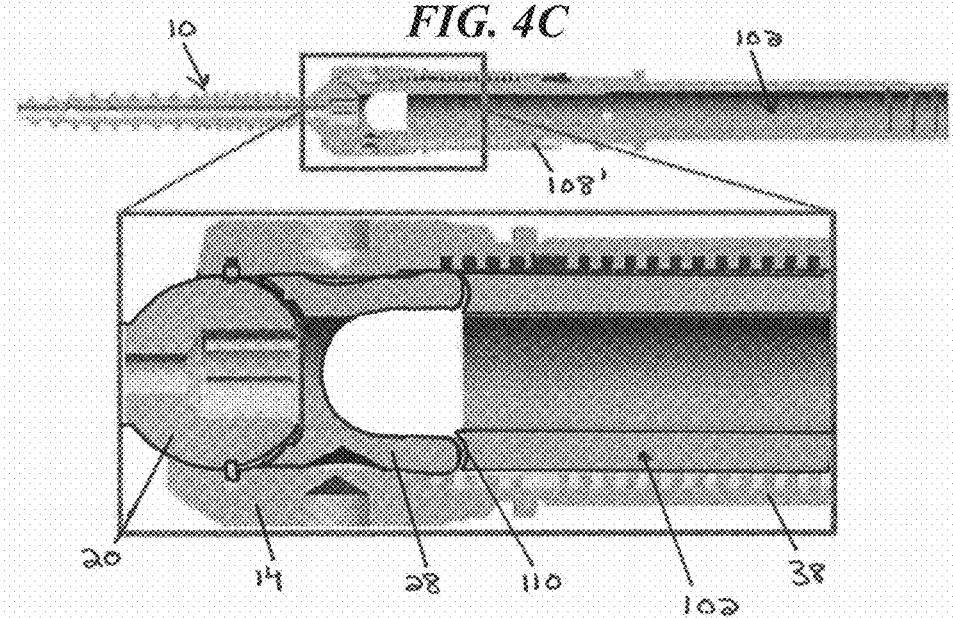
FIG. 4C is a sectional view with magnified inset of the distraction sleeve of FIG. 4A coupled to the bone anchor assembly of FIG. 1A.

In the embodiment of FIGS. 3A-3D, the threaded mating feature 108 for coupling the distraction sleeve 102 to the bone anchor assembly 10 is disposed at a distal-most portion of the sleeve. In other embodiments, however, as shown in FIG. 4A-4C, the threads 108' can be positioned more proximally. In this manner, the sleeve 102 can be fully engaged with the compression member 28 without having to thread the sleeve all the way down the extension tabs 38 and into the receiver member 14, reducing time and surgeon effort. In other words, the sleeve 102 can be bottomed out in the receiver member 14 when the threaded portion 108 is only advanced into a proximal portion of the extension tabs 38. This embodiment can also provide enhanced protection of the extension tabs 38 of the bone anchor assembly 10 by allowing focused tension to be applied towards the strongest aspect of the tabs.

FIGS. 5A-5C illustrate another exemplary embodiment of the distraction sleeve 102 in which the sleeve includes a tubular pocket 118 sized and positioned to receive at least a portion of the extension tabs 38 of a bone anchor assembly 10 when the distraction sleeve is mated to the bone anchor assembly. The pocket 118 can advantageously support the extension tabs 38 to prevent them from splaying outwards as the distraction sleeve 102 is threaded therebetween, and to prevent the tabs from inadvertently separating from the receiver member 14 prematurely. The pocket 118 can be formed integrally in an exterior sidewall of the distraction sleeve 102 as shown, or can be defined between the exterior sidewall of the sleeve 102 and a separate outer component coupled to the sleeve.

Driver Instrument

The driver instrument 104 is shown in more detail in FIGS. 6A-6D. In use, the driver instrument 104 can be selectively coupled to the distraction sleeve 102 and to a bone anchor assembly 10 to allow the bone anchor assembly to be driven into bone while the distraction sleeve is attached thereto. The driver instrument 104 generally includes a driver shaft 120 and a body 122. The body 122 can define a central passage through which the driver shaft 120 is received and in which the driver shaft can rotate relative to the body. A distal portion of the body 122 can include a mating feature for selectively coupling the driver instrument to the distraction sleeve.

The driver shaft 120 can include an elongate cylindrical body having a proximal end 120p and a distal end 120d and extending along a central longitudinal axis L2. The body of the driver shaft 120 can be cannulated to allow passage of a guidewire therethrough. The cannulation can also allow for injection of bone cement or other flowable materials through the driver shaft 120 to a bone anchor assembly 10 coupled thereto.

The proximal end 120p of the driver shaft 120 can include a modular coupling 124 for selectively attaching the driver shaft to a structure or device for applying a rotational force to the driver shaft about the longitudinal axis L2. For example, the modular coupling 124 can be configured to attach the driver shaft 120 to a handle or knob configured to be grasped by a user, to a powered device such as an electric or pneumatic drill or driver, or to a surgical robot. In other embodiments, the driver shaft 120 can include a handle formed integrally therewith.

The distal end 120d of the driver shaft 120 can include a drive tip 126 for engaging a corresponding drive interface of a bone anchor 12 and for transferring rotational force applied to the driver shaft to the bone anchor. Exemplary drive tips include Phillips, slotted, hexalobe, Torx®, hexagonal, pentalobe, and the like, of various standard or non-standard sizes. The drive tip 126 can also include a modular connector such that any of a plurality of drive tips having different types or sizes can be selectively coupled to the distal end of the driver shaft 120.

The driver shaft 120 can also include one or more radial projections or protrusions to facilitate interaction with various components of the body 122, as detailed below. In the illustrated embodiment, the driver shaft 120 includes a radial projection 128. The radial projection 128 can include a proximal-facing surface that is substantially perpendicular to the driver shaft 120 and a distal-facing surface that extends from the driver shaft at an oblique angle.

The body 122 can extend along a central longitudinal axis L3 and can include a distal stem portion 130 and a proximal housing 132 in which a spring 134 is disposed. The stem portion 130 and the proximal housing 132 can collectively define a continuous passage 136 (shown in FIG. 6C) through the body 122 in which the driver shaft 120 can be received. Depending on the operating configuration of the system 100, the driver shaft 120 can be configured to rotate and/or translate longitudinally in various directions within the passage 136. When the instrument is fully-assembled, the central longitudinal axis L2 of the driver shaft 120 can be collinear with the central longitudinal axis L1 of the distraction sleeve 102 and the central longitudinal axis L3 of the body 122.

The proximal housing 132 can define an inner chamber in which the spring 134 is disposed. The spring 134 can have a distal end seated against the radial projection 128 of the driver shaft 120 and a proximal end seated against a retaining cap 138. Once the spring 134 is assembled into the proximal housing 132, the retaining cap 138 can be secured to the housing via a welded, threaded, or other connection. The spring 134 can be effective to bias the body 122 in a proximal, longitudinal direction with respect to the driver shaft 120.

One or more openings can be formed in the sidewall of the housing 132, which can advantageously allow sterilizing solutions, cleaning agents, or other flowable materials to access the interior of the housing. In the illustrated embodiment, the housing 132 includes a faceted sidewall, with each face including at least one opening formed therein. The housing 132 can also include one or more longitudinal grooves to make the housing easier to grip.

The body 122 can include a mating or engagement feature configured to selectively engage the distraction sleeve 102 to couple the driver instrument 104 to the distraction sleeve. The engagement feature can be disposed at any of a variety of locations along the body 122, such as the distal tip of the stem portion 130 as shown. Any of a number of engagement mechanisms can be used. Exemplary mechanisms include a threaded interface, a snap-fit connection, a ball plunger assembly, and the like. In the illustrated embodiment, a spring-loaded bayonet or slot-and-tab coupling is shown in which the stem portion includes one or more U-shaped slots 140 sized and positioned to receive the one or more ears 112 of the distraction sleeve 102. The U-shaped slots can each include a first longitudinal portion 140a that is open to the distal end of the body 122, a second longitudinal portion 140b that is parallel to the first longitudinal portion and closed to the distal end of the body, and a lateral portion 140c connecting the first and second longitudinal portions.

Figure 6A:
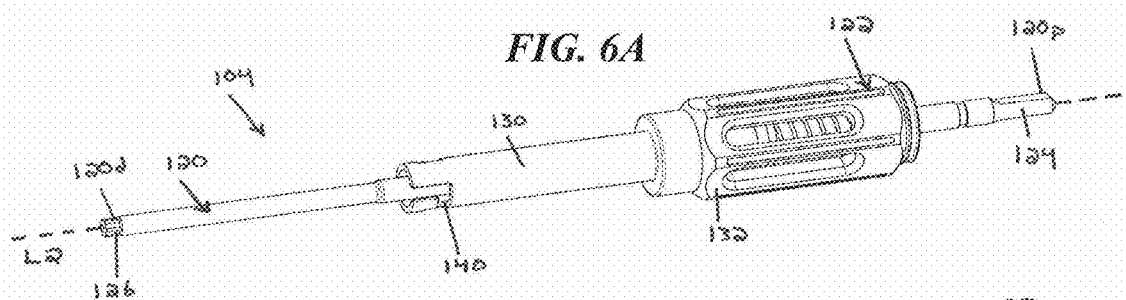
FIG. 6A is a perspective view of a driver instrument.
Figure 6B:
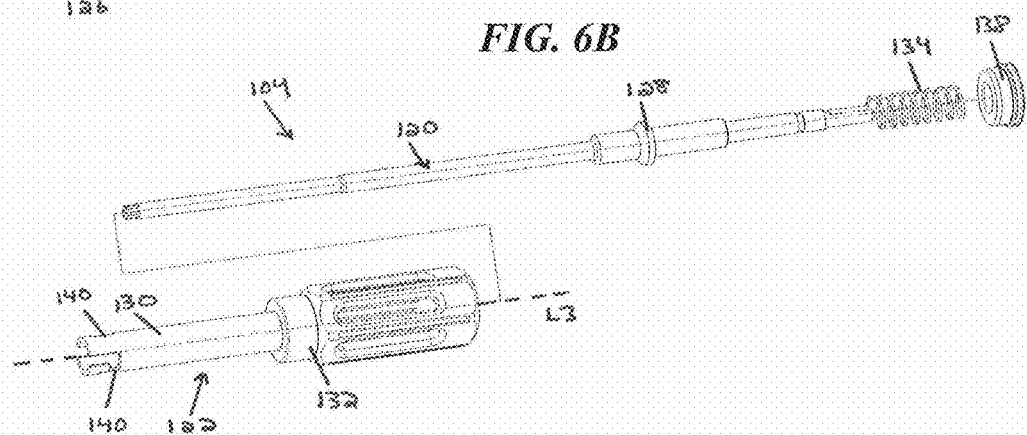
FIG. 6B is an exploded perspective view of the driver instrument of FIG. 6A.
Figure 6C:
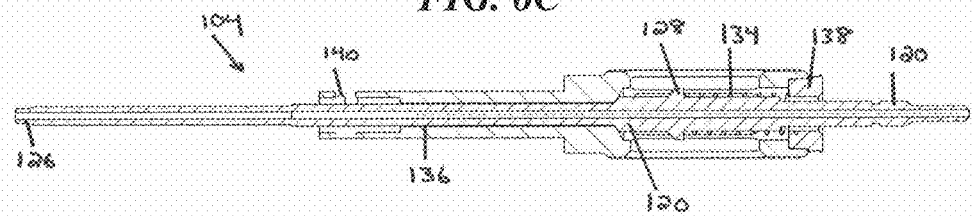
FIG. 6C is a sectional view of the driver instrument of FIG. 6A.
Figure 6D:
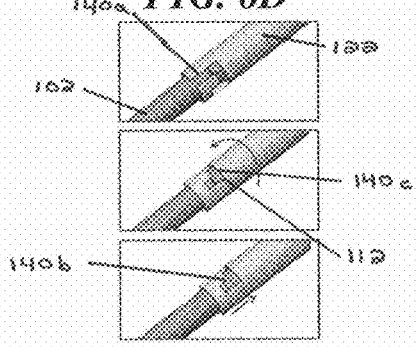
FIG. 6D is a sequence diagram illustrating a process for connecting the driver instrument of FIG. 6A to a distraction sleeve.

In use, the driver shaft 120 can be inserted through the distraction sleeve 102 such that the drive tip 126 engages with the shank 12 of the bone anchor assembly 10 and such that the body 122 can be mated to the distraction sleeve 102. In particular, as shown in FIG. 6D, the body 122 can then be urged distally with respect to the distraction sleeve 102 against the bias of the spring 134 to advance the ears 112 of the distraction sleeve proximally within the open first longitudinal portions 140a of the U-shaped slots 140. The body 122 can then be rotated with respect to the distraction sleeve 102 to advance the ears 112 within the lateral portions 140c of the U-shaped slots 140. Finally, the body 112 can be released to allow the bias of the spring 134 to urge the body 122 proximally with respect to the distraction sleeve 102 to advance the ears 112 distally within the closed second longitudinal portions 140b of the U-shaped slots 140, thereby coupling the driver instrument 104 to the distraction sleeve 102 in a rotationally-fixed manner. The driver instrument 104 can be decoupled from the distraction sleeve 102 by performing the reverse of the above steps.

Torque Instruments

The system 100 can include various instruments for applying a torque to the distraction sleeve 102 to thread the distraction sleeve into the receiver member 14 and compress the compression cap 28 to lock the bone anchor assembly 10, or to remove the distraction sleeve from the receiver member.

Figure 7A:
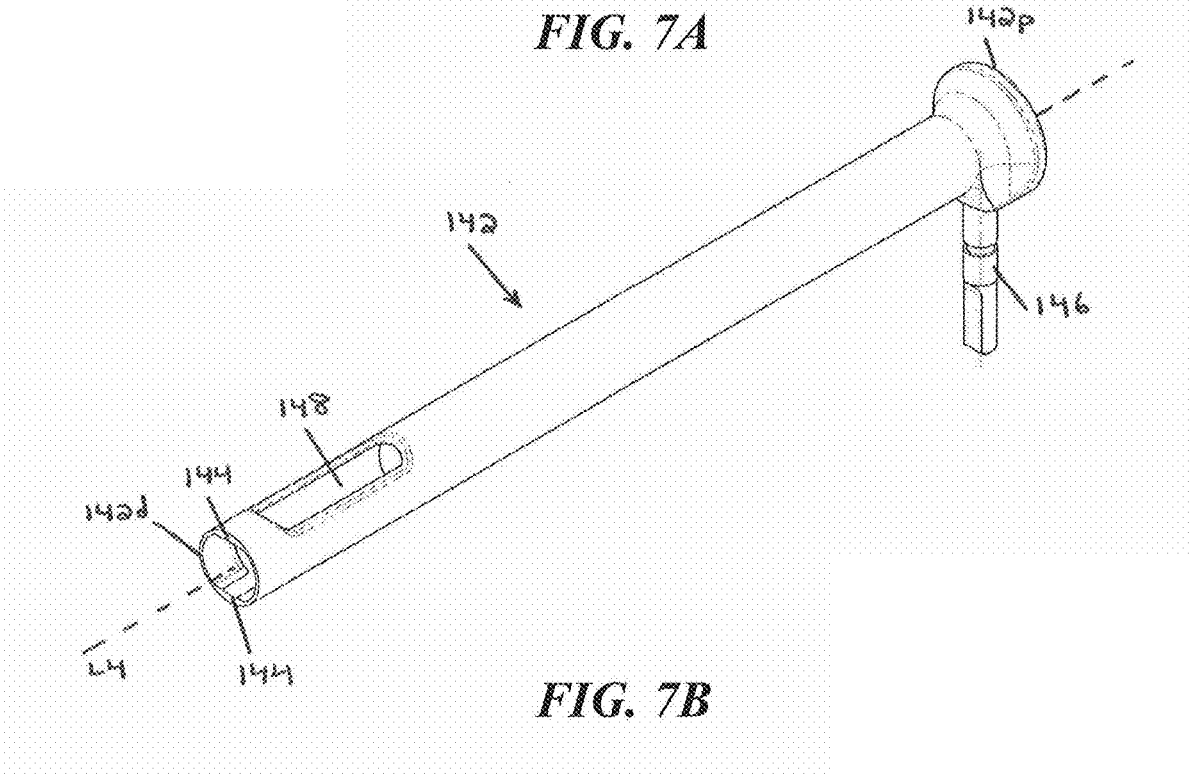
FIG. 7A is a perspective view of a countertorque tube.
Figure 7B:
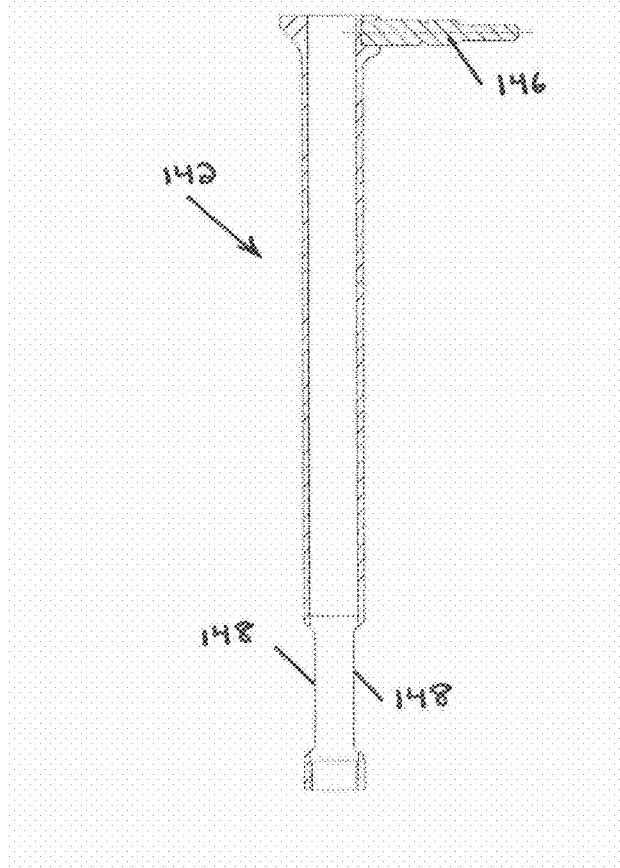
FIG. 7B is a sectional view of the countertorque tube of FIG. 7A.

For example, as shown in FIGS. 7A-7B, the system 100 can include a countertorque tube 142. The countertorque tube 142 can include a generally tubular elongate body configured to slide over the outer sidewall of the distraction sleeve 102 and engage the bone anchor assembly 10 in a rotationally-fixed manner. In the illustrated embodiment, the open distal end 142d of the countertorque tube 142 includes first and second opposed flats 144 configured to engage corresponding flats formed on the receiver member 14 of the bone anchor assembly 10. Thus, when the countertorque tube 142 is mated to the bone anchor assembly 10, the countertorque tube cannot be rotated about its central longitudinal axis L4 with respect to the receiver member 14 of the bone anchor assembly. Accordingly, the countertorque tube 142 can be held stationary while a torque is applied to the distraction sleeve 102 disposed therethrough such that the distraction sleeve can be advanced into or retracted from the receiver member 14 instead of the receiver member just spinning about the shank 12 of the bone anchor assembly 10. It will be appreciated that an alternate technique would be to hold the distraction sleeve 102 stationary and instead rotate the counter torque tube 142 and receiver member 14.

The countertorque tube 142 can have a handle or other gripping features formed thereon to facilitate grasping by a user. Alternatively, or in addition, the countertorque tube 142 can include a modular coupling 146 to which various handles or other components can be coupled. In the illustrated embodiment, the countertorque tube 142 includes a modular coupling 146 that extends laterally from a proximal-most end 142p of the countertorque tube. One or more windows 148 can be included adjacent the distal end 142d of the countertorque tube 142 to allow visualization of the interface between the bone anchor assembly 10 and the distraction sleeve 102.

Figure 8A:
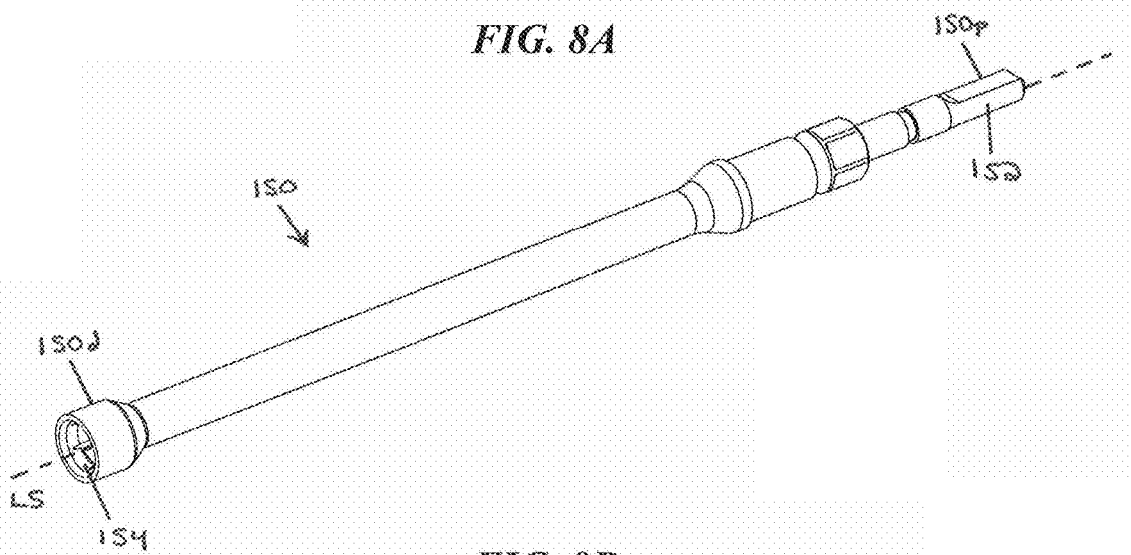
FIG. 8A is a perspective view of a torque wrench.
Figure 8B:
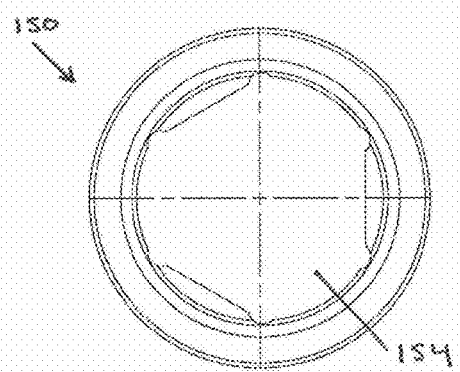
FIG. 8B is a distal end view of the torque wrench of FIG. 8A.

By way of further example, as shown in FIGS. 8A-8B, the system 100 can include a torque wrench 150 for applying torque to the distraction sleeve 102.

The torque wrench 150 can include an elongate cylindrical body having a proximal end 150p and a distal end 150d and extending along a central longitudinal axis L5. The body of the torque wrench 150 can be cannulated to allow passage of a guidewire therethrough. The proximal end 150p of the torque wrench 150 can include a modular coupling 152 for selectively attaching the torque wrench to a structure or device for applying a rotational force to the torque wrench about the longitudinal axis L5. For example, the modular coupling 152 can be configured to attach the torque wrench 150 to a handle or knob configured to be grasped by a user, to a powered device such as an electric or pneumatic drill or driver, or to a surgical robot. In other embodiments, the torque wrench 150 can include a handle formed integrally therewith.

The distal end 150d of the torque wrench 150 can include a drive tip 154 for engaging a corresponding drive interface 114 of the distraction sleeve 102 and for transferring rotational force applied to the torque wrench to the distraction sleeve. Exemplary drive tips include a female tri-lobe tip as shown in FIG. 8B, as well as Phillips, slotted, hexalobe, Torx®, hexagonal, pentalobe, and the like, of various standard or non-standard sizes. The drive tip 154 can also include a modular connector such that any of a plurality of drive tips having different types or sizes can be selectively coupled to the distal end of the torque wrench 150.

In use, the drive tip 154 of the torque wrench 150 can be coupled to the driving interface 114 of the distraction sleeve 102 and the torque wrench can be rotated to advance the distraction sleeve into the receiver member 14 of the bone anchor assembly 10 or to withdraw the distraction sleeve from the receiver member of the bone anchor assembly. In some embodiments, the torque wrench 150 can be used simultaneously with the countertorque tube 142 of FIGS. 7A-7B.

Figure 9A:
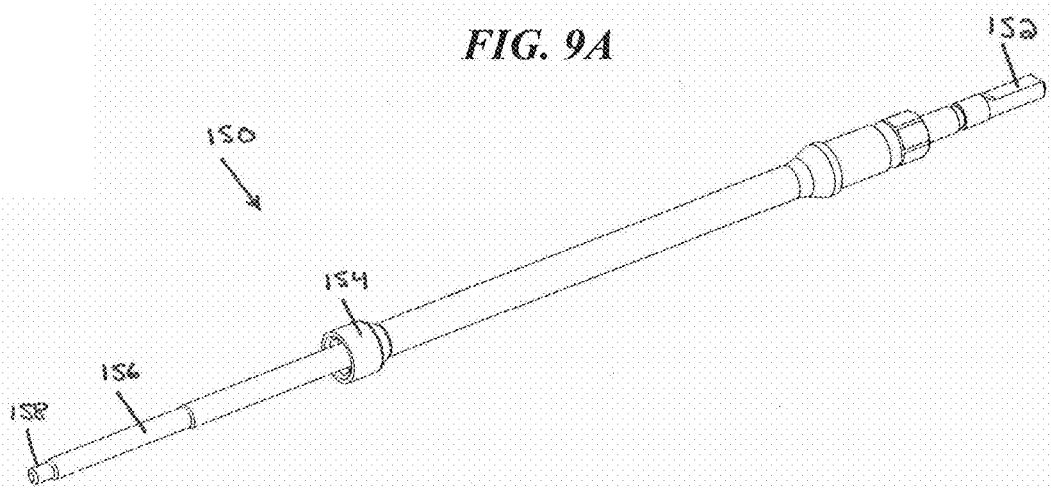
FIG. 9A is a perspective view of a torque wrench.
Figure 9B:
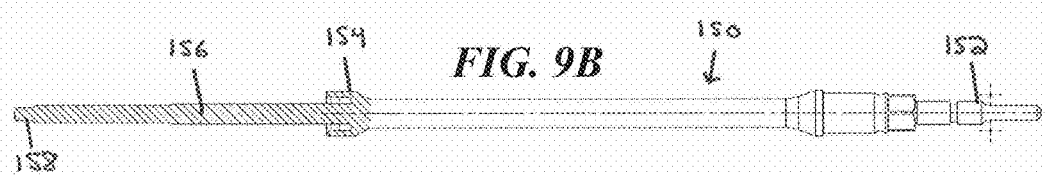
FIG. 9B is a sectional view of the torque wrench of FIG. 9A.
Figure 9C:
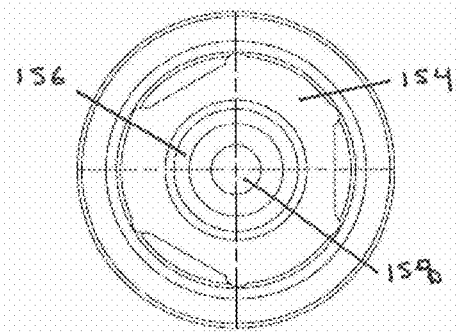
FIG. 9C is a distal end view of the torque wrench of FIG. 9A.

In some embodiments, as shown in FIGS. 9A-9C, the torque wrench 150 can include an alignment pin 156 that extends distally from the drive tip 154. The alignment pin 156 can be formed integrally with the torque wrench 150, or can be a separate component that extends through a cannulation or inner lumen of the torque wrench. A distal end of the alignment pin 156 can include a drive tip 158 configured to mate with the driving interface formed in the head 20 of the bone anchor assembly 10. Accordingly, the alignment pin 156 can be effective to maintain coaxial alignment between the shank 22 of the bone anchor assembly 10, the distraction sleeve 102, and the torque wrench 150. Specifically, when the torque wrench 150 is coupled to the proximal drive end 114 of a distraction sleeve 102 that is in turn coupled at its distal end to a bone anchor assembly 10, the alignment pin 156 of the torque wrench extends through the distraction sleeve and the receiver member 14 to engage the drive interface formed in the head 20 of the bone anchor assembly 10 and maintain alignment between all of said components. Embodiments in which the alignment pin 156 can be removed from or retracted with respect to the torque wrench 150 can advantageously allow the torque wrench to be used when the shank 22 of the bone anchor assembly 10 is not coaxial with the distraction sleeve 102 (e.g., when attaching the distraction sleeve to a previously installed screw with limited operating clearance, when removing the distraction sleeve, etc.).

Protection and Retraction Sheaths

In some embodiments, the system 100 can include a protection sheath and/or a retraction sheath.

Figure 10:
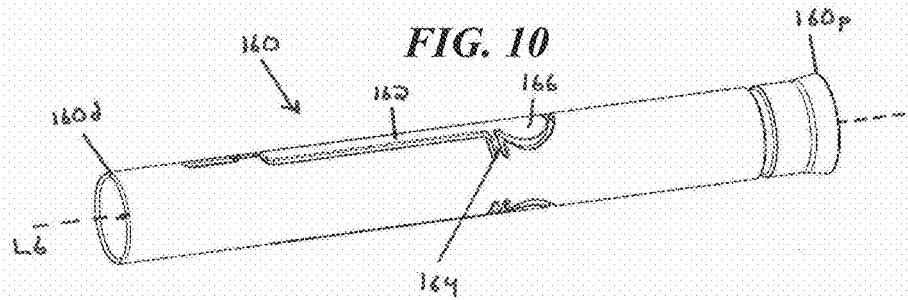
FIG. 10 is a perspective view of a protection sheath.

FIG. 10 illustrates an exemplary embodiment of a protection sheath 160. The sheath 160 can assembled over the outer surfaces of the bone anchor assembly 10, the distraction sleeve 102, and/or the driver instrument 104 to form a protective barrier between patient tissue and components which may rotate during bone anchor installation. This can desirably prevent delicate tissue (e.g., muscle, nerves, vasculature, connective tissue, etc.) from being abraded, cut, tangled, or otherwise damaged by the rotating components.

The protection sheath 160 can include an elongate tubular frame having a proximal end 160p and a distal end 160d and extending along a central longitudinal axis L6. One or both ends of the sheath 160 can be flared or enlarged such that the end has a diameter greater than that of the central portion of the sheath. For example, the sheath 160 can have a flared proximal portion sized to accommodate a corresponding flared portion of the body 122. The flared proximal portion can provide an indication to a user as to the proper orientation of the sheath 160 with respect to the body 122 during assembly of the system 100. By way of further example, the sheath 160 can have a flared distal portion to guide or facilitate insertion of at least a portion of a bone anchor assembly 10 or distraction sheath 102 therein. In other words, the flared distal portion can act as a funnel or lead-in for the proximal end of a bone anchor assembly 10 as it is inserted into the distal end of the sheath 160.

The sheath 160 can also include one or more mating features for coupling the sheath to the distraction sleeve 102 and/or to the body 122. In the illustrated embodiment, the mating features include first and second lever arms 162 having tabs or projections that extend radially-inward therefrom towards the central axis L6 of the sheath 160. The lever arms 162 can be configured to engage corresponding grooves, recesses, or other mating features formed on the distraction sleeve 102 or the body 122. For example, the illustrated lever arms 162 are configured to engage the recess defined between the protrusions 116 of the distraction sleeve 102. The lever arms 162 can be pivoted with respect to the sheath 160 to move the tabs radially inward towards the central passage of the sheath or radially outward away from the central passage of the sheath.

Each lever arm 162 can be a separate component from the sheath 160, or can be formed integrally with the sidewall of the sheath as shown, e.g., by removing material from the sheath to define an outline of the lever arm. A small section of material can be left on each lateral side of the lever arm 162 to define a living hinge 164 that acts as a fulcrum for the lever arm. While removal of material from the sheath 160 is generally described herein, it will be appreciated that the lever arms 162 can be formed by addition of material to the sheath, by molding, or by other processes which will be apparent to one skilled in the art. A portion of the lever arm 162 disposed opposite the fulcrum 164 from the portion of the lever arm from which the tab extends can serve as a button 166 which, when depressed by a user, causes the tab to move radially outward and disengage the distraction sleeve 102 or body 122. The material used to form the fulcrum 164 can have resilient properties such that, when the button portion 166 of the lever arm 162 is released by the user, the tabs can be biased radially inward back towards a position in which they engage the distraction sleeve 102 or the body 122. Other biasing elements, such as coiled or leaf springs, can be included instead or in addition.

Figure 11A:
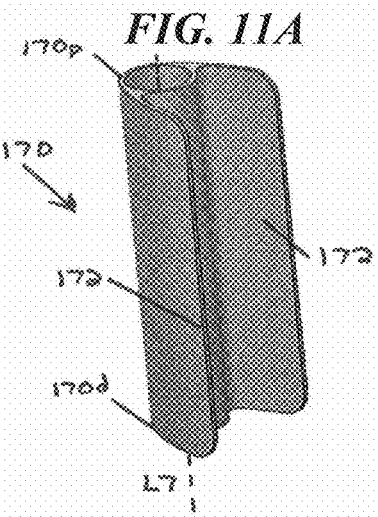
FIG. 11A is a perspective view of a retraction sheath.
Figure 11B:
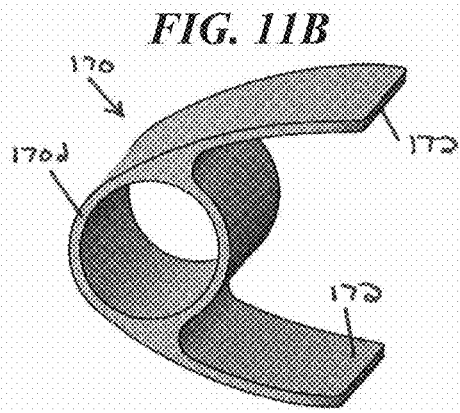
FIG. 11B is a perspective end view of the retraction sheath of FIG. 11A.

FIGS. 11A-11B illustrate an exemplary embodiment of a retraction sheath 170. The sheath 170 can assembled over the outer surfaces of the bone anchor assembly 10, the distraction sleeve 102, and/or the driver instrument 104 to form a protective barrier between patient tissue and components which may rotate during bone anchor installation. This can desirably prevent delicate tissue (e.g., muscle, nerves, vasculature, connective tissue, etc.) from being abraded, cut, tangled, or otherwise damaged by the rotating components. The sheath 170 can also retract a wound opening in which the system 100 is positioned to provide visualization of the surgical site, a working channel for passage of instruments or implants, etc.

The retraction sheath 170 can include an elongate tubular frame having a proximal end 170p and a distal end 170d and extending along a central longitudinal axis L7. One or more wings 172 can project radially outward from the outer sidewall of the frame to act as tissue retraction blades. The wings 172 can extend along the entire length of the sheath 170 or only along a portion thereof. The sheath 170 can be rotated with respect to the bone anchor assembly 10 to orient the wings in the desired direction. For example, when the sheath 170 is disposed over a distraction sleeve 102 coupled to a bone anchor assembly 10 implanted in a vertebra that is superior to the site where a discectomy is to be performed, the sheath can be rotated such that the wings 172 extend in an inferior direction to define a retracted opening adjacent to the bone anchor assembly 10 and over the disc space where the discectomy is to occur. The discectomy can then be performed using the space between the wings 172 as a working channel to the disc space.

Figure 12A:
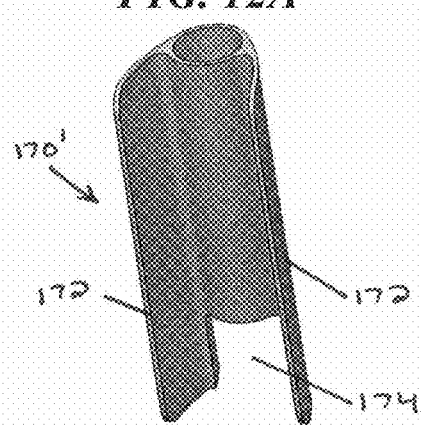
FIG. 12A is a perspective view of a retraction sheath.
Figure 12B:
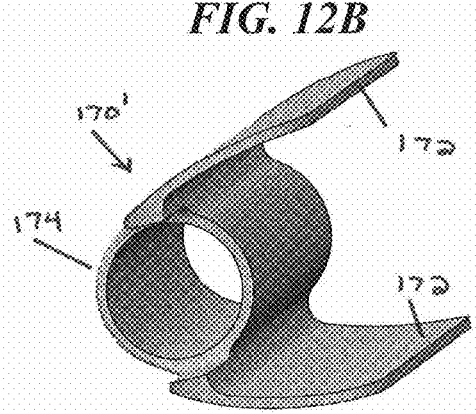
FIG. 12B is a perspective end view of the retraction sheath of FIG. 12A.

FIGS. 12A-12B illustrate another exemplary retraction sheath 170' that includes a cut-out or relief 174 sized to receive at least a portion of a bone anchor assembly 10, such as the receiver member 14. This can advantageously allow the retraction sheath 170' to be slid distally over the distraction sleeve 102 until the distal ends of the wings 172 bottom out against the bone in which the bone anchor assembly 10 is implanted.

Figure 13A:
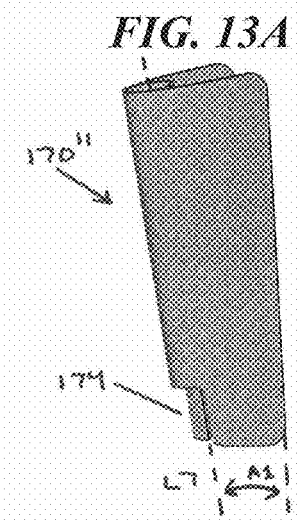
FIG. 13A is a perspective view of a retraction sheath.
Figure 13B:
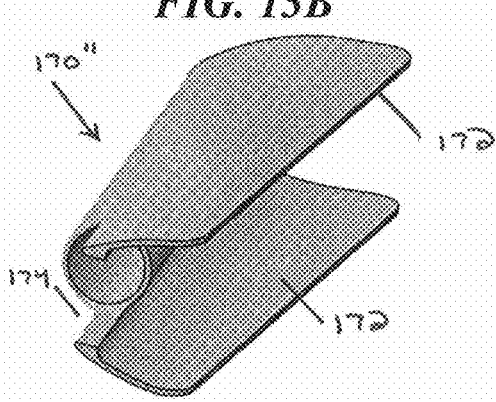
FIG. 13B is a perspective end view of the retraction sheath of FIG. 13A.

FIGS. 13A-13B illustrate another exemplary retraction sheath 170" in which the free lateral ends of the wings 172 are non-parallel to the central longitudinal axis L7 of the tubular frame of the sheath. For example, the ends of the wings can extend at an oblique angle A1 with respect to the longitudinal axis L7 of the sheath 170". This can advantageously allow the sheath 170" to define a broader working channel, to position the driver instrument 104 or other component coupled to the bone anchor assembly 10 out of the way of the working channel, or to allow the sheath to be used when the bone anchor assembly or driver is placed in different orientations.

Methods

FIGS. 14A-14K schematically illustrate an exemplary method of using the systems disclosed herein.

Figure 14A:
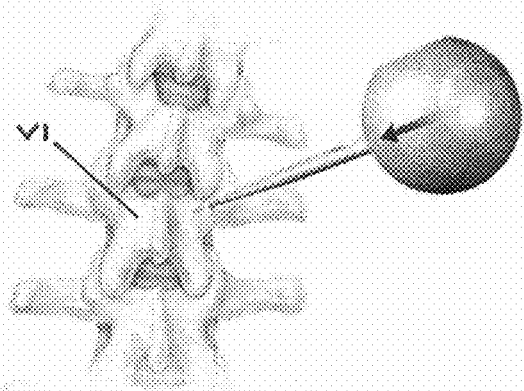

The procedure can begin by forming an open or percutaneous incision in the patient to access a bone in which a bone anchor assembly 10 is to be implanted. The bone can be prepared to receive the bone anchor assembly 10 as known in the art. In FIG. 14A, a pedicle of a vertebra V1 is prepared using standard awl, probe, and tap steps.

Figure 14B:
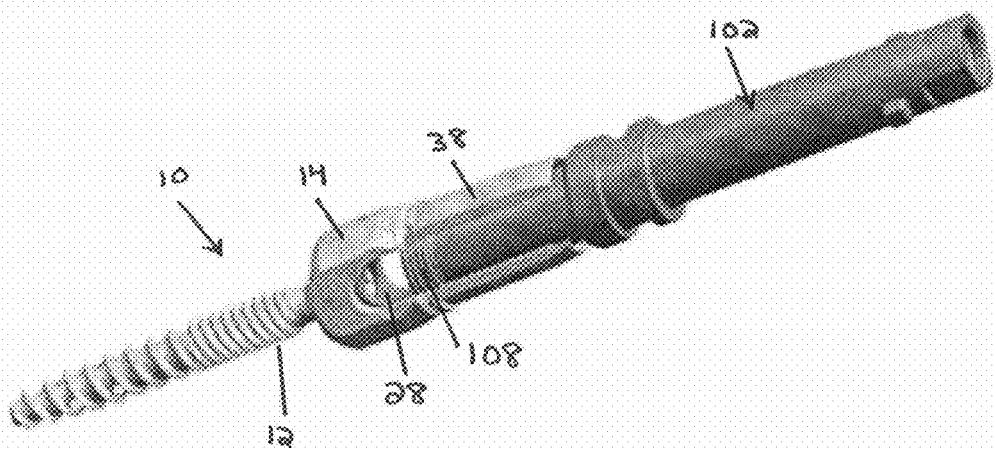

Before or after preparing the bone, the distraction sleeve 102 can be coupled to the bone anchor assembly 10 that is to be implanted in the patient, as shown in FIG. 14B. For example, the threaded distal end 108 of the distraction sleeve 102 can be engaged with the threaded extension tabs 38 of the bone anchor assembly 10 and the distraction sleeve can be rotated about its longitudinal axis with respect to the bone anchor assembly to advance the distraction sleeve into contact with the compression cap 28. Continued rotation of the distraction sleeve 102 can be performed to compress the compression cap 28 against the head of the bone anchor 12 to lock off the polyaxial degree of freedom of the bone anchor assembly 10 or at least provide increased resistance to polyaxial movement of the bone anchor assembly.

Figure 14C:
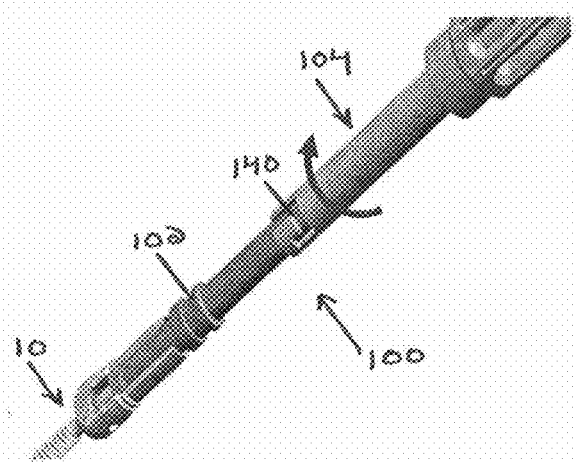

As shown in FIG. 14C, the driver instrument 104 can be coupled to the distraction sleeve 102 and the bone anchor assembly 10. In particular, the outer shaft 122 of the driver instrument 104 can be slid over the distraction sleeve 102 to align a cam-lock or other mating feature 140. The driver instrument 104 can then be advanced distally, rotated, and released to lock the driver instrument to the distraction sleeve 102. As the driver instrument 104 is advanced over the distraction sleeve 102, the drive tip 126 of the driver shaft 120 can be inserted into the drive interface of the bone anchor 12. If needed, the distraction sleeve 102 can be threaded back slightly to allow for partial movement of the bone anchor 12 to accommodate appropriate axial alignment before being re-tightened to lock off the polyaxial degree of freedom.

Figure 14D:
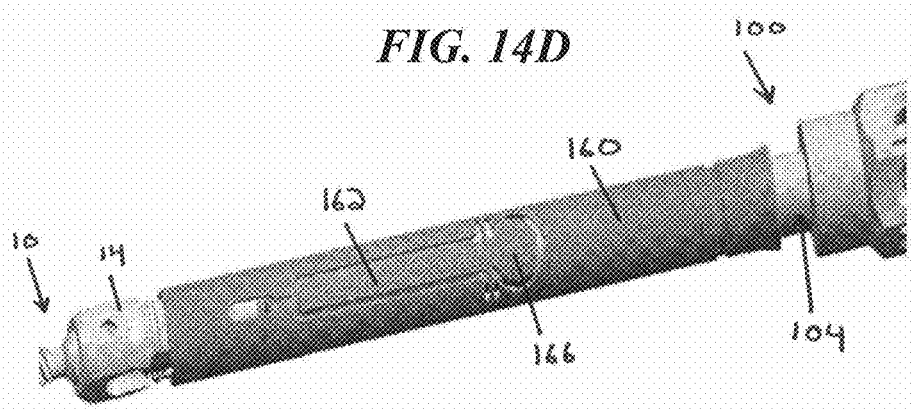

As shown in FIG. 14D, a protection sheath 160 or a retraction sheath 170, 170', 170" can be installed over one or more components of the system 100 to protect and/or retract nearby tissue. The sheath 160 can also allow the instrument to be held distally, improving stability as the bone anchor assembly 10 is advanced into the bone V1. The sheath 160 can be rotatably coupled to the distraction sleeve 102 and/or the driver instrument 104 such that the sheath can remain stationary relative to the patient while the distraction sleeve and/or the driver instrument are rotated relative to the patient. In the illustrated embodiment, a protection sheath 160 is shown attached to the instrument by depressing the release lever buttons 166, sliding the sheath 160 towards the driver instrument 104 handle, and releasing the release lever buttons to allow the levers 162 to snap into engagement with a feature on the distraction sleeve 102. For clarity, the protection sheath 160 is not shown in subsequent drawings, though it can be present or absent in any of the steps illustrated by those drawings.

With the instrument assembled as described above, or at any intermediate stage of assembly, the bone anchor assembly 10 can be passed through the incision formed in the patient, brought into contact with the prepared bone V1, and rotated to drive the shank 22 of the bone anchor assembly 10 into the bone. In particular, the driver shaft 120 of the driver instrument 104 can be rotated to advance the bone anchor 12 into the bone V1.

Figure 14E:
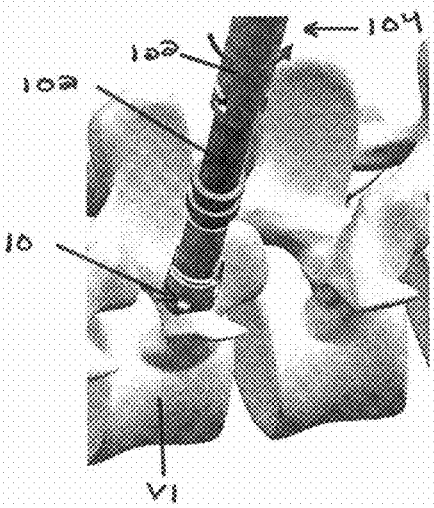
Figure 14F:
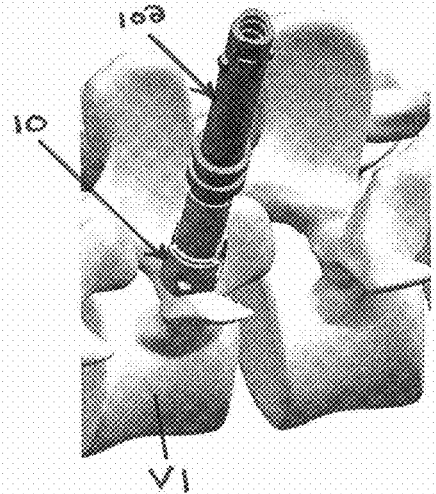

Once the bone anchor assembly 10 is at least partially implanted in the bone V1, or at any other desired time, the driver instrument 104 can be disconnected from the distraction sleeve 102. As shown in FIG. 14E, the user can push the body portion 122 of the driver instrument 104 distally, rotate the body portion relative to the distraction sleeve 102, and release the body portion to allow the spring 134 to urge the body portion proximally off of the ears 112 of the distraction sleeve, thereby separating the components. With the driver instrument 104 removed, the installed bone anchor assembly 10 and attached distraction sleeve 102 are left in place, as shown in FIG. 14F. Since the distraction sleeve 102 remains seated against the compression cap 28, the polyaxial degree of freedom of the bone anchor assembly 10 remains locked such that the construct can facilitate true parallel distraction of the vertebrae.

Figure 14G:
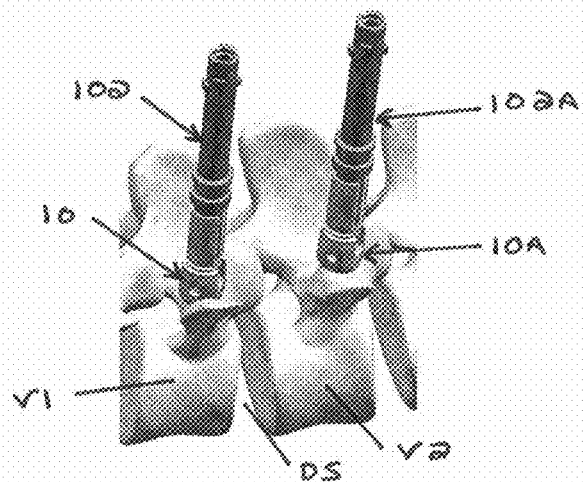

The above steps can be repeated to install additional bone anchor assemblies at the same or at different vertebral levels. In FIG. 14G, a first bone anchor assembly 10 and accompanying distraction sleeve 102 are shown installed in a first, inferior vertebra V1 and a second bone anchor assembly 10A and accompanying distraction sleeve 102A are shown installed in a second, superior vertebra V2.

Figure 14H:
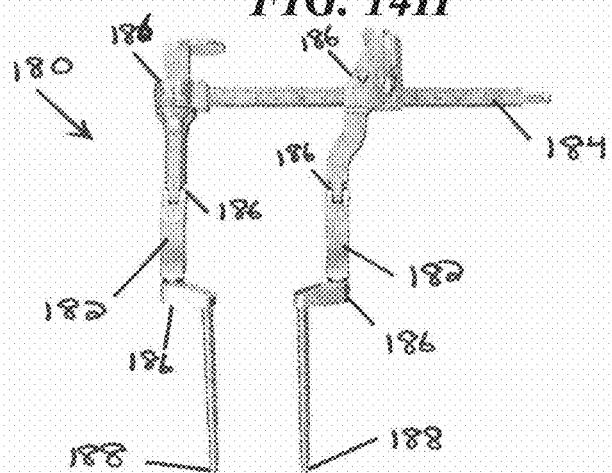

With bone anchor assemblies 10, 10A and corresponding distraction sleeves 102, 102A positioned on opposite sides of the target disc space DS, a distractor instrument 180 can be coupled to the distraction sleeves to distract the disc space. FIG. 14H illustrates an exemplary distractor instrument 180 that includes first and second legs 182 mounted on a rack 184. The position and orientation of the legs 182 with respect to the rack 184 can be adjusted in one or more degrees of freedom via a plurality of joints 186. The distal tips 188 of the distraction legs 182 can include a drive tip that corresponds with the driving interface formed in the head 20 of the bone anchor assembly 10, such that when the legs 182 are inserted through the distraction sleeves 102, 102A, the drive tips engage the driving interface of the bone anchor assemblies 10, 10A.

Figure 14I:
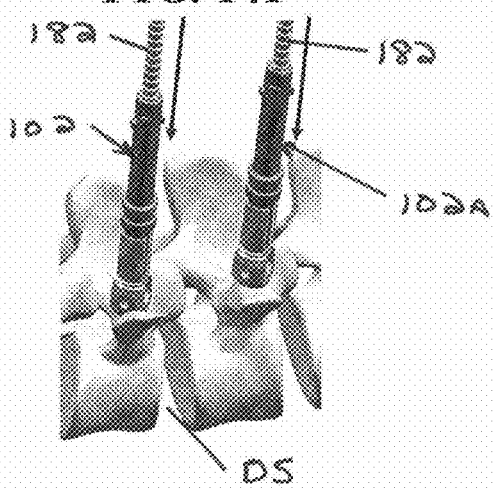

As shown in FIG. 14I, the legs 182 of the distractor 180 can be slid distally into the distraction sleeves 102, 102A. The legs 182 can be advanced until they bottom out on the proximal surface of the distraction sleeves 102, 102A, or until the drive tips 188 of the legs bottom out in the driving interface of the bone anchor assemblies 10, 10A. Once seated in the distraction sleeves 102, 102A, the distractor instrument 180 can be actuated to distract the disc space DS. Because the polyaxial degree of freedom of the bone anchor assemblies 10, 10A is locked by the distraction sleeves 102, 102A, true parallel distraction can be achieved. In other words, the vertebral endplates on either side of the disc space DS can remain at a fixed angle (parallel or non-parallel) with respect to one another as the disc space is distracted.

With the disc space DS adequately distracted, any desired procedure can be performed with respect to the disc space as known in the art. For example, a curette or other tool can be used to perform a discectomy and then a fusion cage, bone graft, or motion-preserving disc replacement implant can be inserted into the disc space DS.

Figure 14J:
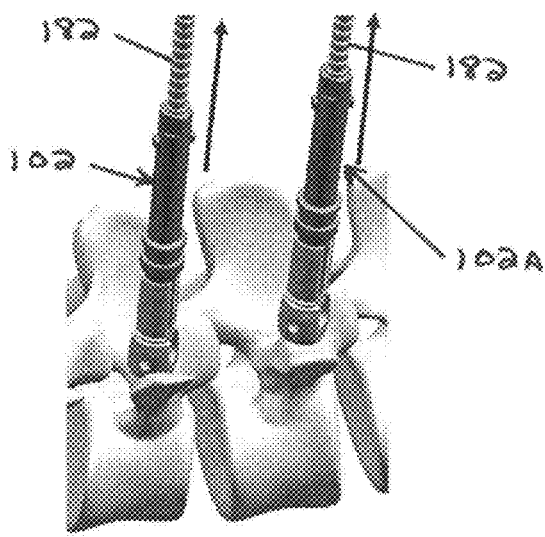

Once the disc space DS is stabilized, the distractor instrument 180 can be removed by sliding the legs 182 of the distractor proximally out of the distraction sleeves 102, 102A as shown in FIG. 14J.

Figure 14K:
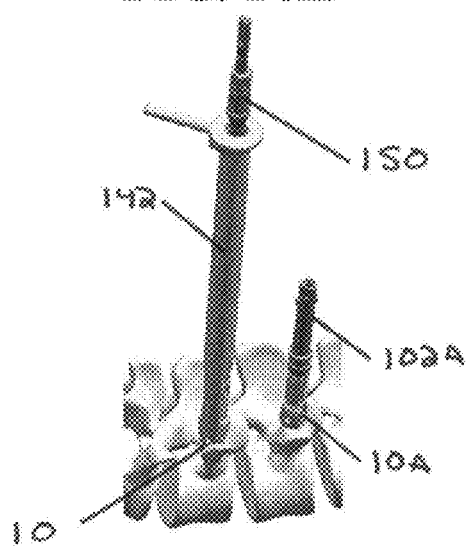

The distraction sleeves 102, 102A can be removed from the bone anchor assemblies 10, 10A using the countertorque tube 142 and torque wrench 150 as shown in FIG. 14K. In particular, the countertorque tube 142 can be slid distally over the outside of the distraction sleeve 102 and engaged with the bone anchor assembly 10 such that the countertorque tube is rotationally fixed with respect to the receiver member 14 of the bone anchor assembly. While holding the countertorque tube 142 stationary via an attached modular handle, the torque wrench 150 can be engaged with the driving interface 114 of the distraction sleeve 102 and rotated to back the distraction sleeve out of the bone anchor assembly 10 and release the compression cap 28 to restore the polyaxial degree of freedom of the receiver member 14.

A spinal fixation element (e.g., a spinal rod 16) can then be seated in the receiver members 14 of one or more bone anchor assemblies 10 and closure mechanisms 18 can be applied to secure the rod and/or lock the polyaxial movement of the bone anchor assemblies. The procedure can be completed using known techniques and the incision closed.

While the method illustrated and described herein involves distraction, it will be appreciated that the systems and methods herein can be used for compression, rotation, fracture reduction, and any of a variety of other types of bone manipulation. In addition, while the method illustrated and described herein involves bone anchors placed in the pedicle or lateral mass of vertebral bone, it will be appreciated that the systems and methods herein can be used in any bone or even non-bone tissue.

In some embodiments, the countertorque tube and torque wrench can be used when initially attaching the distraction sleeves to the bone anchor assemblies. In some embodiments, the bone anchor assemblies can be implanted in bone first, before attaching the distraction sleeves to the bone anchor assemblies. For example, the distraction sleeve can be attached to a bone anchor assembly previously installed in the same surgical procedure or, in the case of revision surgery, during a previous surgical procedure.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

As evident from the foregoing, in at least some embodiments, the systems and methods disclosed herein can provide one or more advantages as compared with other systems and methods:

The systems and methods can allow the polyaxial degree of freedom of the bone anchor assembly to be locked or limited without directly engaging the shank and/or head of the bone anchor assembly, without directly engaging the exterior of the receiver member of the bone anchor assembly, and/or without installing a spinal rod or closure mechanism in the bone anchor assembly.

The systems and methods can allow for true parallel distraction of a disc space. Parallel distraction allows for equal posterior and anterior distraction which can advantageously provide more complete distraction for more complete discectomy. Similarly, the systems and methods can allow for true parallel compression which can advantageously provide more even distribution of compression forces over a cage or graft.

The systems and methods can allow for streamlined, combined bone anchor insertion and distraction sleeve loading.

The systems and methods can allow for bone anchors to be inserted such that they are ready to receive a distraction instrument immediately upon insertion.

The systems and methods can allow a distraction sleeve to be coupled to a bone anchor assembly with an embedded option of locking off the polyaxial degree of freedom of the bone anchor assembly.

The systems and methods can allow a pre-loaded distraction sleeve to be used with a protection or retraction sheath.

The instruments disclosed herein and the various component parts thereof can be constructed from any of a variety of known materials. Exemplary materials include those which are suitable for use in surgical applications, including metals such as stainless steel, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The systems and methods disclosed herein can be used in minimally-invasive surgery and/or open surgery. While the systems and methods disclosed herein are generally described in the context spinal surgery, it will be appreciated that the systems and methods disclosed herein can be used with any human or animal implant, in any of a variety of surgeries performed on humans or animals, and/or in fields unrelated to implants or surgery.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A bone manipulation system, comprising:
a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element; and
a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument;
wherein the distraction sleeve includes an external thread that threads into an internal thread of first and second opposed extension tabs that extend proximally from the receiver member and wherein the external thread is spaced a distance apart from the distal end of the distraction sleeve such that the external thread engages proximal ends of the extension tabs when the distal end of the distraction sleeve is seated in the receiver member.

2. The system of claim 1, wherein a distal-facing surface of the distraction sleeve engages proximal-facing surfaces of the first and second arms of the compression cap when the sleeve is seated in the receiver member.

3. The system of claim 2, wherein the distal-facing surface of the distraction sleeve has a concave longitudinal cross-section that corresponds with a convex longitudinal cross-section of the first and second arms of the compression cap.

4. The system of claim 1, wherein the distraction sleeve has a length sufficient to extend to a skin surface of a patient when the distal end of the distraction sleeve is seated in the receiver member and the bone anchor is implanted in a bone of the patient.

5. The system of claim 1, wherein the distraction sleeve includes an external thread that threads into an internal thread of the receiver member.

6. The system of claim 1, wherein the extension tabs have free proximal ends and define a slot therebetween through which a rod can be reduced into the receiver member.

7. The system of claim 1, wherein the distraction sleeve includes a tubular pocket sized and positioned to receive at least a portion of each extension tab when the distal end of the distraction sleeve is seated in the receiver member.

8. The system of claim 7, wherein the external thread is formed within the tubular pocket.

9. The system of claim 1, further comprising a driver instrument that includes:
a driver shaft insertable through the distraction sleeve and the receiver member and having a distal drive tip configured to engage the bone anchor for driving the bone anchor into bone; and
a body portion in which the driver shaft is rotatably disposed, the body portion having a mating feature configured to engage a corresponding mating feature of the distraction sleeve to selectively couple the body portion to the distraction sleeve.

10. The system of claim 9, wherein the mating feature of the body portion comprises at least one slot and the mating feature of the distraction sleeve comprises at least one projection that extends radially outward from the distraction sleeve.

11. The system of claim 10, wherein the at least one slot comprises a first longitudinal portion open to a distal end of the body portion, a second longitudinal portion that is closed to the distal end of the body portion, and a lateral portion connecting the first and second longitudinal portions.

12. The system of claim 9, wherein the body portion houses a spring configured to bias the body portion proximally with respect to the driver shaft.

13. The system of claim 1, further comprising a torque wrench having a drive tip configured to engage a driving interface of the distraction sleeve and an alignment pin that extends distally from the drive tip to engage a driving interface formed in the bone anchor when the torque wrench is coupled to the distraction sleeve and the distraction sleeve is coupled to the bone anchor assembly.

14. The system of claim 1, further comprising a retraction sheath having a tubular frame rotatably disposed over an external surface of the distraction sleeve and having at least one wing extending laterally from the tubular frame to retract tissue.

15. The system of claim 14, wherein the at least one wing comprises first and second wings that define a working channel therebetween.

16. The system of claim 14, wherein the tubular frame includes a relief sized to accommodate the receiver member of the bone anchor assembly such that the at least one wing of the retraction sheath extends at least to a distal end of the receiver member when the retraction sheath is installed over the receiver member.

17. A bone manipulation system, comprising:
a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element; and
a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument;
wherein the distraction sleeve includes an external thread that threads into an internal thread of first and second opposed extension tabs that extend proximally from the receiver member and wherein the distraction sleeve includes a tubular pocket sized and positioned to receive at least a portion of each extension tab when the distal end of the distraction sleeve is seated in the receiver member.

18. The system of claim 17, wherein the external thread is formed within the tubular pocket.

19. A bone manipulation system, comprising:
a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element;
a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument; and
a driver instrument that includes:
a driver shaft insertable through the distraction sleeve and the receiver member and having a distal drive tip configured to engage the bone anchor for driving the bone anchor into bone; and
a body portion in which the driver shaft is rotatably disposed, the body portion having a mating feature configured to engage a corresponding mating feature of the distraction sleeve to selectively couple the body portion to the distraction sleeve;
wherein the mating feature of the body portion comprises at least one slot and the mating feature of the distraction sleeve comprises at least one projection that extends radially outward from the distraction sleeve and wherein the at least one slot comprises a first longitudinal portion open to a distal end of the body portion, a second longitudinal portion that is closed to the distal end of the body portion, and a lateral portion connecting the first and second longitudinal portions.

20. A bone manipulation system, comprising:
a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element; and
a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument;
a driver instrument that includes:
a driver shaft insertable through the distraction sleeve and the receiver member and having a distal drive tip configured to engage the bone anchor for driving the bone anchor into bone; and
a body portion in which the driver shaft is rotatably disposed, the body portion having a mating feature configured to engage a corresponding mating feature of the distraction sleeve to selectively couple the body portion to the distraction sleeve;
wherein the body portion houses a spring configured to bias the body portion proximally with respect to the driver shaft.

21. A bone manipulation system, comprising:
a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element;
a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument; and
a torque wrench having a drive tip configured to engage a driving interface of the distraction sleeve and an alignment pin that extends distally from the drive tip to engage a driving interface formed in the bone anchor when the torque wrench is coupled to the distraction sleeve and the distraction sleeve is coupled to the bone anchor assembly.

22. A bone manipulation system, comprising:
a bone anchor assembly that includes a bone anchor implantable in bone, a receiver member that is movable relative to the bone anchor, and a compression cap that, when advanced distally within the receiver member, engages the bone anchor to limit or prevent movement between the bone anchor and the receiver member, the compression cap having first and second arms that define a recess therebetween for receiving a spinal fixation element;
a distraction sleeve having an elongate tubular body with a distal end that engages the first and second arms of the compression cap as the sleeve is advanced into the receiver member to urge the compression cap distally, wherein the distal end of the distraction sleeve rotates relative to the receiver member as the sleeve is advanced into the receiver member and wherein a proximal end of the distraction sleeve protrudes from the receiver member and defines an inner lumen for receiving an instrument; and
a retraction sheath having a tubular frame rotatably disposed over an external surface of the distraction sleeve and having at least one wing extending laterally from the tubular frame to retract tissue.

23. The system of claim 22, wherein the at least one wing comprises first and second wings that define a working channel therebetween.

24. The system of claim 22, wherein the tubular frame includes a relief sized to accommodate the receiver member of the bone anchor assembly such that the at least one wing of the retraction sheath extends at least to a distal end of the receiver member when the retraction sheath is installed over the receiver member.

* * * * *